(12) United States Patent
Lee et al.

(10) Patent No.: US 9,573,985 B2
(45) Date of Patent: Feb. 21, 2017

(54) P16 PROTEIN VARIANT AND USE THEREOF FOR PREVENTING OR TREATING CANCER

(71) Applicant: Samsung Electronics Co., Ltd., Suwon-si, Gyeonggi-do (KR)

(72) Inventors: Jung-Hoon Lee, Hwaseong-si (KR); Eunji Kang, Gyeonggi-do (KR); Jung Min Kim, Seoul (KR); Jung-Min Lee, Suwon-si (KR); Jae Il Lee, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 70 days.

(21) Appl. No.: 14/615,146

(22) Filed: Feb. 5, 2015

(65) Prior Publication Data

US 2015/0218240 A1    Aug. 6, 2015

(30) Foreign Application Priority Data

Feb. 5, 2014   (KR) .................. 10-2014-0013238

(51) Int. Cl.
*C07K 14/47* (2006.01)
*A61K 38/00* (2006.01)

(52) U.S. Cl.
CPC .......... *C07K 14/4738* (2013.01); *A61K 38/00* (2013.01)

(58) Field of Classification Search
CPC ................................. C07K 14/4738
See application file for complete search history.

(56) References Cited

U.S. PATENT DOCUMENTS

| | | | |
|---|---|---|---|
| 6,033,847 | A | 3/2000 | Sherr et al. |
| 7,550,561 | B1 | 6/2009 | Beach et al. |
| 8,110,653 | B2 | 2/2012 | Stumpp et al. |
| 2010/0305041 | A1 | 12/2010 | Jo et al. |

FOREIGN PATENT DOCUMENTS

KR    100887266 B1    2/2009

OTHER PUBLICATIONS

Byeon et al., "Tumor Suppressor p16 $I^{NK4A}$: Determination of Solution Structure and Analyses of Its Interaction with Cyclin-Dependent Kinase 4", *Molecular Cell*, 1:421-431 (1998).

*Primary Examiner* — Amber D Steele
(74) *Attorney, Agent, or Firm* — Leydig, Voit & Mayer, Ltd.

(57) ABSTRACT

A p16 protein variant; a polynucleotide encoding the p16 protein variant; a method for preparing the p16 protein variant; a pharmaceutical composition comprising the p16 protein variant; a method for preventing and/or treating cancer comprising administering the p16 protein variant to a subject; and use of the p16 protein variant in the prophylaxis and/or therapy of cancer.

17 Claims, 7 Drawing Sheets

FIG. 6

```
mouse_p16    ----------MESAADRLARAAAQGRVHDVRALLEAGVSPNAPNSFGRTPIQVMMMGNVHVA
(SEQ ID NO:5)
rat_p16      ----------MESSADRLARAAALGREHEVRALLEAGASPNAPNTFGRTPIQVMMMGNVKVA
(SEQ ID NO:6)
human_p16    MEPAAGSSMEPSADWLATAAARGRVEEVRALLEAGALPNAPNSYGRRPIQVMMMGSARVA
(SEQ ID NO:1)
             *:.:**  ** *** ** .:*:**:************.:**

mouse_p16    ALLINYGADSNCEDPTTFSRPVHDAAREGFLDTLVVLHGSGARLDVRDAWGRLPLDLAQE
rat_p16      ALLLSYGADSNCEDPTTLSRPVHDAAREGFLDTLVVLHQAGARLDVRDAWGRLPLDLALE
human_p16    ELLLHGAEPNCADPATLTRPVHDAAREGFLDTLVVLHRAGARLDVRDAWGRLPVDLAEE
             *  :: *  **:* :************* :*******:*. * mouse_p16    RGHQDIVRYLRSAGCSLCSAGWSLCTAGNVAQTDG-HSFSSSTPRALELRGQSQEQS
rat_p16      RGHHDVVRYLR------------YLLSSAGNVSRVTDRHNFCSSTPRCLGLRGQPPKQR
human_p16    LGHRDVARYLR------------AAAGGTRGSNHARIDAAEGPSDIPD----------
             ***:*:****              .: *  .. :. * * :
```

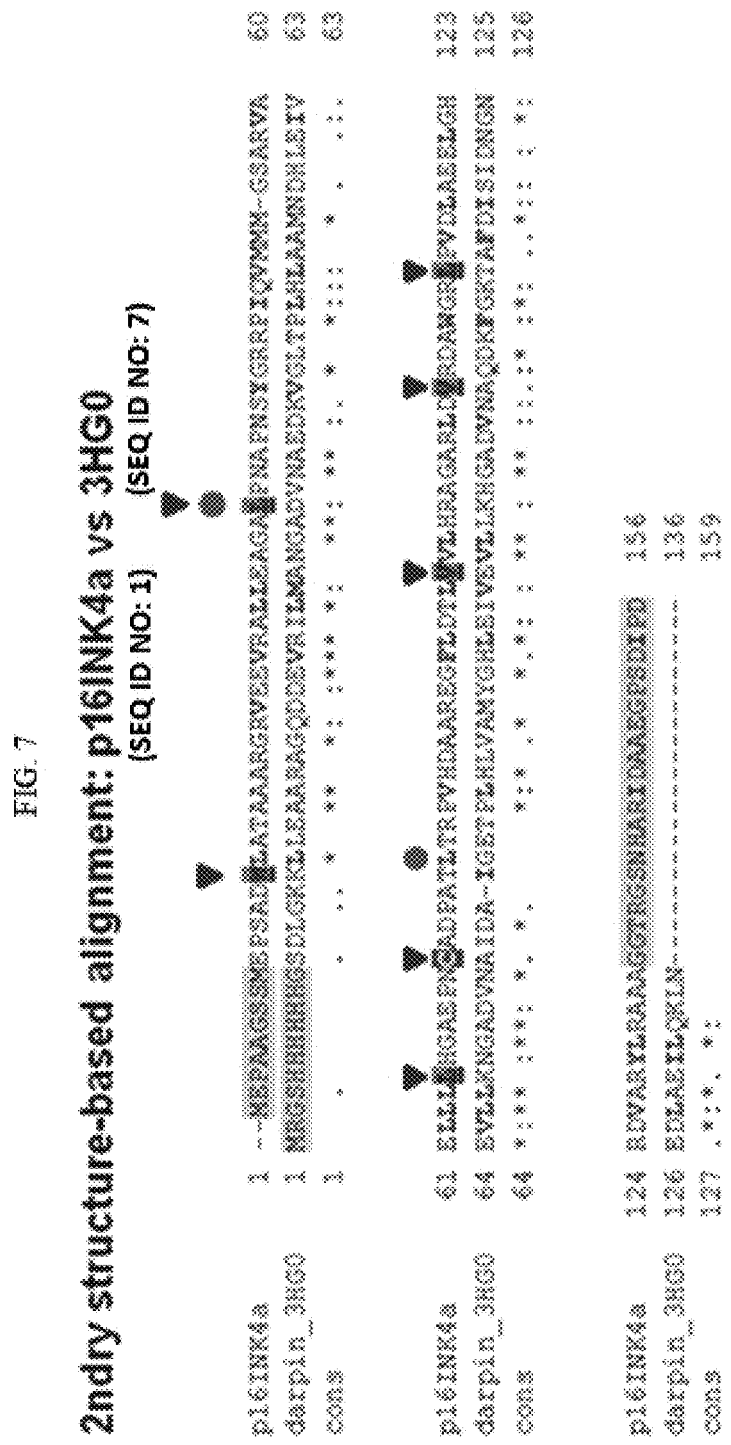

P16 PROTEIN VARIANT AND USE THEREOF FOR PREVENTING OR TREATING CANCER

CROSS-REFERENCE TO RELATED APPLICATIONS

This application claims the benefit of Korean Patent Application No. 10-2014-0013238 filed on Feb. 5, 2014 in the Korean Intellectual Property Office, the entire disclosure of which is hereby incorporated by reference.

INCORPORATION BY REFERENCE OF ELECTRONICALLY SUBMITTED MATERIALS

Incorporated by reference in its entirety herein is a computer-readable nucleotide/amino acid sequence listing submitted herewith and identified as follows: One 26,773 bytes ASCII (Text) file named "719223_ST25.TXT," created Feb. 5, 2015.

BACKGROUND OF THE INVENTION

1. Field

Provided is a p16 protein variant; a polynucleotide encoding the p16 protein variant; a method for preparing the p16 protein variant; a pharmaceutical composition comprising the p16 protein variant; and a method for preventing and/or treating cancer comprising administering the p16 protein variant to a subject.

2. Description of the Related Art $p16^{INK4a}$ (hereinafter abbreviated as "p16") plays an important role in cell cycle regulation by decelerating the cell-cycle progression from the gap one phase ($G_1$) to the DNA synthesis (S) phase (i.e., $G_1 \rightarrow S$), a major check point (restriction point) responsible for the division of both normal and cancer cells. More specifically, p16 protein binds to cyclin-dependent kinase 4/6 (Cdk4/6) to arrest cell proliferation (see, FIG. 1).

When p16 protein binds to Cdk4/6, the cell cycle progression from $G_1$ phase to S phase ($G_1 \rightarrow S$) is restricted, which, in turn, prohibits the subsequent events for cancer development including DNA synthesis in S phase and infinite cell division. Therefore, p16 protein can be effectively used as a tumor suppressor.

For cancer therapy using p16, delivery into cancer cells requires modification to provide a recombinant p16 with improved cell membrane permeability. However, human p16 protein is difficult to produce on a mass scale in *E. coli* because it is expressed as an insoluble form in *E. coli*. Solubility of p16 may be increased by fusion with GST. However recombinant GST-p16, although expressed and/or isolated, becomes unstable and undergoes precipitation (Byeon, I. J. et al., 1998. *Mol. Cell* 421-431).

Thus, there is a need for a p16 protein variant with improved solubility that retains affinity for Cdk4/6, to provide for the effective application of p16 in cancer therapy.

BRIEF SUMMARY OF THE INVENTION

An embodiment provides a p16 protein variant. The p16 protein variant may have improved water-solubility as compared to native human p16, while retaining affinity for Cdk4/6. In one embodiment, the p16 protein variant includes a substitution wherein at least one hydrophobic amino acid residue that is exposed on the tertiary structure of a p16 protein is substituted with a hydrophilic amino acid. In another embodiment, the p16 protein includes a variant of SEQ ID NO: 1, 5, or 6 in which at least one exposed hydrophobic amino acid residue on the tertiary structure of a p16 protein is substituted with a hydrophilic amino acid.

Another embodiment provides a polynucleotide encoding the p16 protein variant.

Another embodiment provides a pharmaceutical composition including the p16 protein variant as an active ingredient.

Another embodiment provides a method of preventing and/or treating cancer, including administering the p16 protein variant to a subject in need thereof.

Another embodiment provides a method of preparing a p16 protein variant by providing a polypeptide having a variant of a p16 amino acid sequence in which amino acid residues exposed externally on the three-dimensional structure of p16 are substituted.

Also provided is a method of increasing solubility of a p15(INK4b), p16(INK4a), p18(INK4c), or p19(INK4d), the method including comparing solvent-exposed regions of the p15(INK4b), p16(INK4a), p18(INK4c), or p19(INK4d) protein and a reference designed ankyrin repeat protein (DARPin) comprising 4 or 5 ankyrin repeat motifs through secondary or tertiary structure-based alignment; identifying a position of the solvent exposed region of the p15(INK4b), p16(INK4a), p18(INK4c), or p19(INK4d) protein where the p15(INK4b), p16(INK4a), p18(INK4c), or p19(INK4d) protein has a hydrophobic amino acid while the reference DARPin protein has a hydrophilic amino acid at a corresponding position; and substituting the hydrophobic amino acid at the position in the protein of interest with a hydrophilic amino acid.

BRIEF DESCRIPTION OF THE DRAWINGS

FIG. 6 is an alignment of amino acid sequences among a human p16 protein, a mouse p16 protein, and a rat p16 protein (CLUSTAL 2.1 multiple sequence alignment).

FIG. 7 is a secondary structure-based alignment between human p16 protein (SEQ ID NO: 1) and a DARPin (PDB 3HGO; SEQ ID NO: 7).

DETAILED DESCRIPTION OF THE INVENTION

Figure 1:
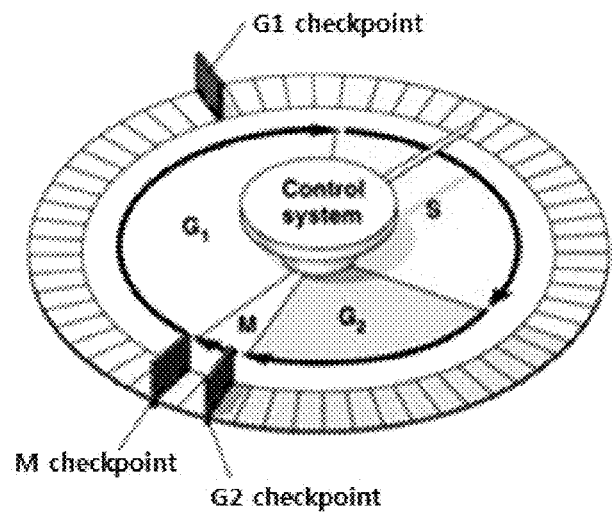
FIG. 1 is a schematic illustrating a cell cycle and three check points.

Intensive and thorough research into the application of p16 to cancer therapy resulted in the finding that: when an amino acid at a position such that it is exposed externally (e.g., to aqueous environment) on the three-dimensional structure of p16 and is not responsible for binding to Cdk4/6 is substituted by a hydrophilic amino acid residue, the resulting p16 protein variant is improved in solubility, with the retention of affinity for Cdk4/6.

An embodiment provides a p16 protein variant. The p16 protein variant is characterized by an improvement in solubility, with the retention of affinity for Cdk4/6, through a mutation (e.g., substitution) on at least one selected from amino acids at such positions that they are exposed externally (e.g., to aqueous environment) on the three dimensional structure of the intact protein and not responsible for binding to Cdk4/6.

p16 is a cyclin-dependent kinase (CDK) inhibitor functioning to arrest the cell cycle by inactivating CDKs that phosphorylate retinoblastoma protein (Rb). With this function, p16 contributes to prevent the infinite division of cells to the development of cancer cells, and therefor acts as a tumor suppressor.

The p16 protein may be originated from mammals including primates, such as humans, monkeys and the like; and rodents, such as mice, rat, and the like. For example, the p16 may be a human p16 protein (SEQ ID NO: 1), a mouse p16 protein (SEQ ID NO: 5), or a rat p16 protein (SEQ ID NO: 6).

The p16 protein variant may be provided by mutation of at least one amino acid on the amino acid sequence of p16 protein; wherein the at least one amino acid is a hydrophobic residue at a position externally exposed on the three dimensional structure of the protein in aqueous solution and is not responsible for binding to CDKs (e.g., Cdk4/6). The term "position externally exposed on the three dimensional structure of the protein" may refer to a position of the protein in aqueous solution in contact with a solvent (e.g., an aqueous solvent) or aqueous environment when the protein is formulated or administered into a body. As used herein, the term "mutation" employed in association with amino acid sequences of p16 may refer to substitution of at least one amino acid with a different amino acid(s), for example, a change from a hydrophobic amino acid(s) to a hydrophilic amino acid(s), wherein the hydrophobic amino acid may be selected from the group consisting of leucine, cysteine, valine, phenyl alanine, tryptophan, isoleucine, proline, methionine, and a combination thereof and the hydrophilic amino acid is selected from the group consisting of lysine (K), aspartic acid (D), glutamic acid (E), glutamine (Q), asparagine (N), serine (S), alanine (A), threonine (T), arginine (R), and a combination thereof.

In an embodiment, the p16 protein variant may consist of about 100 to about 200 amino acids or about 150 to about 170 amino acids, for example, about 156 amino acids, about 168 amino acids, or about 159 amino acids, and comprise or consist essentially of a polypeptide of SEQ ID NO: 18. The polypeptide of SEQ ID NO: 18 may have an amino acid sequence identity of at least about 60%, at least about 65%, at least about 70%, or at least about 72%, with a part of a wild-type p16 protein (e.g., a region of positions 15 to 113 of human p16 protein (SEQ ID NO: 1) or a region of positions 1 to 105 of a mouse wild-type p16 protein (SEQ ID NO: 5) or rat wild-type p16 protein (SEQ ID NO: 6)). In the p16 protein variant comprising SEQ ID NO: 18, the remaining part except the polypeptide of SEQ ID NO: 18 may comprise or consist essentially of any amino acids, for example, the amino acids identical (about 100%) to the corresponding region of a wild-type p16 protein; that is, the p16 protein variant may be obtained by substituting the region of positions 15 to 113 of human p16 protein of SEQ ID NO: 1 or the region of positions 1 to 105 of a mouse wild-type p16 protein of SEQ ID NO: 5 or rat wild-type p16 protein of SEQ ID NO: 6, with SEQ ID NO: 18.

```
                                                      [SEQ ID NO: 18]
X1LAX2AAAX3GR X4X5X6VRALLEA GX7X8PNAPNX9X10             30

GRX11PIQVMMM GX12X13X14VAX15LLL                        60
X16X17GAX18X19NX20X21D

PX22TX23X24RPVHD AAREGFLDTL VVLHX25X26GARL             90

DX27RDAWGRX28                                          99
``` wherein, $X_1$, which corresponds to tryptophan at position 15 (W15) of SEQ ID NO: 1 or an amino acid at position 7 of SEQ ID NO: 5 or SEQ ID NO: 6, is a hydrophilic amino acid or tryptophan (W), for example, lysine (K), arginine (R), aspartic acid (D), glutamic acid (E), glutamine (Q), asparagine (N), serine (S), or tryptophan (W), $X_2$ is threonine (T) or arginine (R);

$X_3$ is arginine (R), glutamine (Q), or leucine (L)

$X_4$ is valine (V) or glutamic acid (E);

$X_5$ is glutamic acid (E) or histidine (H);

$X_6$ is glutamic acid (E) or aspartic acid (D);

$X_7$ is alanine (A) or valine (V);

$X_8$, which corresponds to leucine at position 37 (L37) of SEQ ID NO: 1 or an amino acid at position 29 of SEQ ID NO: 5 or SEQ ID NO: 6, is a hydrophilic amino acid or leucine (L), for example, aspartic acid (D), arginine (R), lysine (K), glutamic acid (E), glutamine (Q), serine (S), asparagine (N), or leucine (L);

$X_9$ is serine (S) or threonine (T);

$X_{10}$ is tyrosine (Y) or phenylalanine (F);

$X_{11}$ is arginine (R) or threonine (T);

$X_{12}$ is serine (S) or asparagine (N);

$X_{13}$ is alanine (A) or valine (V);

$X_{14}$ is arginine (R), histidine (H), or lysine (K);

$X_{15}$ is glutamic acid (E) or alanine (A)

$X_{16}$, which corresponds to leucine at position 65 (L65) of SEQ ID NO: 1 or an amino acid at position 57 of SEQ ID NO: 5 or SEQ ID NO: 6, is a hydrophilic amino acid or leucine (L), for example, aspartic acid (D), arginine (R), lysine (K), glutamic acid (E), glutamine (Q), serine (S), asparagine (N), or leucine (L);

$X_{17}$ is histidine (H) or tyrosine (Y);

$X_{18}$ is glutamic acid (E) or aspartic acid (D);

$X_{19}$ is proline (P) or serine (S);

$X_{20}$, which corresponds to cysteine at position 72 (C72) of SEQ ID NO: 1 or an amino acid at position 64 of SEQ ID NO: 5 or SEQ ID NO: 6, is a hydrophilic amino acid or cysteine (C), for example, serine (S) or cysteine (C);

$X_{21}$ is alanine (A) or glutamic acid (E);

$X_{22}$ is alanine (A) or threonine (T);

$X_{23}$, which corresponds to leucine at position 78 (L78) of SEQ ID NO: 1 or an amino acid at position 70 of SEQ ID NO: 5 or SEQ ID NO: 6, is a hydrophilic amino acid, leucine (L), or phenylalanine (F), for example, serine (S), arginine (R), lysine (K), aspartic acid (D), glutamic acid (E), glutamine (Q), asparagine (N), leucine (L), or phenylalanine (F);

$X_{24}$ is threonine (T) or serine (S);

$X_{25}$ is arginine (R), glycine (G), or glutamine (Q);

$X_{26}$ is alanine (A) or serine (S);

$X_{27}$, which corresponds to valine at position 106 (V106) of SEQ ID NO: 1 or an amino acid at position 98 of SEQ ID NO: 5 or SEQ ID NO: 6, is a hydrophilic amino acid or valine (V), for example, alanine (A), aspartic acid (D), glutamic acid (E), glutamine (Q), asparagine (N), or valine (V); and $X_{28}$, which corresponds to leucine at position 113 (L113) of SEQ ID NO: 1 or an amino acid at position 105 of SEQ ID NO: 5 or SEQ ID NO: 6, is a hydrophilic amino acid or leucine (L), for example, threonine (T), arginine (R), lysine (K), aspartic acid (D), glutamic acid (E), glutamine (Q), asparagine (N), serine (S), or leucine (L).

In SEQ ID NO: 18, the hydrophilic amino acid is selected from the group consisting of lysine (K), aspartic acid (D), glutamic acid (E), glutamine (Q), asparagine (N), serine (S), alanine (A), threonine (T), arginine (R), and a combination thereof. In addition, in SEQ ID NO: 18, at least one of $X_{20}$, $X_1$, $X_{16}$, $X_{28}$, $X_8$, $X_{23}$, and $X_{27}$, for example, at least one of $X_{20}$, $X_1$, $X_{16}$, and $X_{28}$, or at least $X_{20}$, is independently selected from hydrophilic amino acids as listed above, for example, including serine (S), lysine (K), aspartic acid (D), glutamic acid (E), glutamine (Q), asparagine (N), alanine (A), threonine (T), and arginine (R), for example, including serine (S), lysine (K), aspartic acid (D) alanine (A), threonine (T), arginine (R), and asparagine (N) (e.g., $X_{20}$ is serine (S); and/or $X_1$ is lysine (K), arginine (R), aspartic acid (D), glutamic acid (E), glutamine (Q), asparagine (N), or serine (S); and/or $X_{16}$ is aspartic acid (D), arginine (R), lysine (K), glutamic acid (E), glutamine (Q), serine (S), or asparagine (N); and/or $X_{28}$ is threonine (T), arginine (R), lysine (K), aspartic acid (D), glutamic acid (E), glutamine (Q), asparagine (N), or serine (S); and/or $X_8$ is aspartic acid (D), arginine (R), lysine (K), glutamic acid (E), glutamine (Q), serine (S), or asparagine (N); and/or $X_{23}$ is serine (S), arginine (R), lysine (K), aspartic acid (D), glutamic acid (E), glutamine (Q), or asparagine (N); and/or $X_{27}$ is alanine (A), aspartic acid (D), glutamic acid (E), glutamine (Q), or asparagine (N), as described above).

On a wild-type p16 protein, for example, the human p16 protein comprising the amino acid sequence of SEQ ID NO: 1, the amino acid position to undergo such mutation (e.g., substitution) may be at least one selected from the group consisting of tryptophan at position 15 (W15), leucine at position 37 (L37), leucine at position 65 (L65), cysteine at position 72 (C72), leucine at position 78 (L78), valine at position 106 (V106), and leucine at position 113 (L113). W15, L65, C72, and L113 are found to have great influence on the solubility of the protein encoded by SEQ ID NO. 1. The mutation (e.g., substitution), therefore, may occur on at least one amino acid residue selected from the group consisting of W15, L65, C72, L113, or any combination thereof; and optionally, may additionally occur on at least one amino acid residue selected from the group consisting of L37, L78, and V106, or any combination thereof. Thus, the recombinant p16 protein variant can comprise such a sequence.

Suitable amino acid residues to be substituted on the amino acid sequence of SEQ ID NO: 1 are as shown in bold and underlined, below:

```
Wild-Type Human p16
                                        (SEQ ID NO: 1)
MEPAAGSSME PSADWLATAA ARGRVEEVRA LLEAGALPNA

PNSYGRRPIQ VMMMGSARVA ELLLLHGAEP NCADPATLTR

PVHDAAREGF LDTLVVLHRA GARLDVRDAW GRLPVDLAEE

LGHRDVARYL RAAAGGTRGS NHARIDAAEG PSDIPD
```

(possible amino acid residues to undergo substitution are shown in bold and underline)

The amino acid to be substituted on the human p16 protein may be at least one selected from the group consisting of tryptophan at position 15(W15), leucine at position 37 (L37), leucine at position 65 (L65), cysteine at position 72 (C72), leucine at position 78 (L78), valine at position 106 (V106), and leucine at position 113 (L113), or any combination thereof. For example, the amino acid to be substituted on the human P16 protein may be at least one selected from the group consisting of W15, L65, C72, and L113, and optionally, may be further selected from the group consisting of L37, L78, and V106. These amino acids are hydrophobic residues exposed externally (i.e., to the a solvent) on the three-dimensional structure of p16 protein, and may be substituted with hydrophilic amino acids such as negatively or positively charged amino acids or polar amino acids.

The p16 protein variant may be prepared by substituting at least one selected from the group consisting of the above amino acid residues of SEQ ID NO: 1, that is, tryptophan at position 15 (W15), leucine at position 37 (L37), leucine at position 65 (L65), cysteine at position 72 (C72), leucine at position 78 (L78), valine at position 106 (V106), and leucine at position 113 (L113), independently with lysine (K), aspartic acid (D), glutamic acid (E), glutamine (Q), asparagine (N), serine (S), alanine (A), threonine (T), or arginine (R). In order to increase the solubility of the protein, the variant may essentially comprise a substitution of cysteine at position 72 (C72) (e.g., substitution with serine (S)). To achieve better improvement in solubility, substitution of at least one (or at least 2 or all three) selected from leucine at position 37(L37) (e.g., substitution with aspartic acid (D)), leucine at position 78 (L78) (e.g., substitution with serine (S)), and valine at position 106 (V106) (e.g., substitution with alanine (A)), may be in combination with one or more additional substitutions (e.g., substitution of at least one of tryptophan at position 15 (W15), leucine at position 65 (L65), cysteine at position 72 (C72), leucine at position 113 (L113), or combination thereof with a hydrophilic amino acid).

In further detail, the p16 protein variant may comprise SEQ ID NO: 1 in which at least one of tryptophan at position 15 (W15), leucine at position 65 (L65), cysteine at position 72 (C72), and leucine at position 113 (L113), is independently substituted with lysine (K), aspartic acid (D), glutamic acid (E), glutamine (Q), asparagine (N), serine (S), alanine (A), threonine (T), or arginine (R); and optionally, at least one of leucine at position 37 (L37), leucine at position 78(L78), and valine at position 106 (V106) is independently substituted with lysine (K), aspartic acid (D), glutamic acid (E), glutamine (Q), asparagine (N), serine (S), alanine (A), threonine (T), or arginine (R).

For example, the p16 protein variant may comprise SEQ ID NO: 1 including at least one of the following mutations:

a substitution of tryptophan at position 15 (W15) of SEQ ID NO: 1 with lysine (K), arginine (R), aspartic acid (D), glutamic acid (E), glutamine (Q), asparagine (N), or serine (S), a substitution of leucine at position 37 (L37) of SEQ ID NO: 1 with aspartic acid (D), arginine (R), lysine (K), glutamic acid (E), glutamine (Q), serine (S), or asparagine (N), a substitution of leucine at position 65 (L65) of SEQ ID NO: 1 with lysine (K), arginine (R), aspartic acid (D), glutamic acid (E), glutamine (Q), asparagine (N), or serine (S), a substitution of cysteine at position 72 (C72) of SEQ ID NO: 1 with serine (S), a substitution of leucine at position 78 (L78) of SEQ ID NO: 1 with serine (S), arginine (R), lysine (K), aspartic acid (D), glutamic acid (E), glutamine (Q), or asparagine (N), a substitution of valine at position 106 (V106) of SEQ ID NO: 1 with alanine (A), aspartic acid (D), glutamic acid (E), glutamine (Q), or asparagine (N), and a substitution of leucine at position 113 (L113) of SEQ ID NO: 1 with threonine (T), arginine (R), lysine (K), aspartic acid (D), glutamic acid (E), glutamine (Q), asparagine (N), or serine (S).

Out of the viable amino acid residues for a substitution mutation, cysteine at position 72 (C72) may act as a factor to decrease the solubility of the protein by forming an inter-chain disulfide bridge with an adjacent amino acid. Therefore, the p16 protein variant may essentially comprise a mutation of the cysteine at position 72 (C72) corresponding to the amino acid sequence of SEQ ID NO: 1. By way of example, the p16 protein variant may essentially comprise a substitution of the cysteine at position 72 (C72) of SEQ ID NO: 1 with, e.g., serine (S).

In further detail, the p16 protein variant may comprise a substitution of the cysteine at position 72 (C72) of SEQ ID NO: 1 with serine (S) either alone or optionally in combination with at least one mutation of an amino acid of SEQ ID NO: 1 selected from the group consisting of:

a substitution of tryptophan at position 15 (W15) with lysine (K) arginine (R), aspartic acid (D), glutamic acid (E), glutamine (Q), asparagine (N), or serine (S), a substitution of leucine at position 37 (L37) with aspartic acid (D), arginine (R), lysine (K), glutamic acid (E), glutamine (Q), serine (S), or asparagine (N), a substitution of leucine at position 65 (L65) with lysine (K), arginine (R), aspartic acid (D), glutamic acid (E), glutamine (Q), asparagine (N), or serine (S), a substitution of leucine at position 78 (L78) with serine (S), arginine (R), lysine (K), aspartic acid (D), glutamic acid (E), glutamine (Q), or asparagine (N), a substitution of valine at position 106 (V106) with alanine (A), aspartic acid (D), glutamic acid (E), glutamine (Q), or asparagine (N), and a substitution of leucine at position 113 (L113) with threonine (T), arginine (R), lysine (K), aspartic acid (D), glutamic acid (E), glutamine (Q), asparagine (N), or serine (S).

In one embodiment, in addition to the mutation on C72, the p16 protein variant may further comprise at least one mutation selected from the group consisting of:

a substitution of tryptophan at position 15 (W15) of SEQ ID NO: 1 with lysine (K), arginine (R), aspartic acid (D), glutamic acid (E), glutamine (Q), asparagine (N), or serine (S), a substitution of leucine at position 65 (L65) of SEQ ID NO: 1 with lysine (K), arginine (R), aspartic acid (D), glutamic acid (E), glutamine (Q), asparagine (N), or serine (S), and a substitution of leucine at position 113 (L113) of SEQ ID NO: 1 with threonine (T), arginine (R), lysine (K), aspartic acid (D), glutamic acid (E), glutamine (Q), asparagine (N), or serine (S).

In another embodiment, in addition to the mutation on C72 of SEQ ID NO: 1 and at least one amino acid selected from the group consisting of W15, L65, and L113 as described above, the p16 protein variant may further comprise at least one mutation selected from the group consisting of:

a substitution of leucine at position 37 (L37) of SEQ ID NO: 1 with aspartic acid (D), arginine (R), lysine (K), glutamic acid (E), glutamine (Q), serine (S), or asparagine (N), a substitution of leucine at position 78 (L78) of SEQ ID NO: 1 with serine (S), arginine (R), lysine (K), aspartic acid (D), glutamic acid (E), glutamine (Q), or asparagine (N), and a substitution of valine at position 106 (V106) of SEQ ID NO: 1 with alanine (A), aspartic acid (D), glutamic acid (E), glutamine (Q), or asparagine (N).

In a further embodiment, the p16 protein variant may comprise all of the following substitutions: tryptophan at position 15 (W15) with lysine (K), arginine (R), aspartic acid (D), glutamic acid (E), glutamine (Q), asparagine (N), or serine (S), a substitution of leucine at position 37(L37) with aspartic acid (D), arginine (R), lysine (K), glutamic acid (E), glutamine (Q), serine (S), or asparagine (N), a substitution of leucine at position 65 (L65) with lysine (K), arginine (R), aspartic acid (D), glutamic acid (E), glutamine (Q), asparagine (N), or serine (S), a substitution of cysteine at position 72(C72) with serine (S), a substitution of leucine at position 78 (L78) with serine (S), arginine (R), lysine (K), aspartic acid (D), glutamic acid (E), glutamine (Q), or asparagine (N), a substitution of valine at position 106 (V106) with alanine (A), aspartic acid (D), glutamic acid (E), glutamine (Q), or asparagine (N), and a substitution of leucine at position 113 (L113) with threonine (T), arginine (R), lysine (K), aspartic acid (D), glutamic acid (E), glutamine (Q), asparagine (N), or serine (S), on the amino acid sequence of SEQ ID NO: 1 (see, e.g., SEQ ID NO: 2).

```
Human p16 variant
                                      (SEQ ID NO: 2)
MEPAAGSSME PSADKLATAA ARGRVEEVRA LLEAGADPNA

PNSYGRRPIQ VMMMGSARVA ELLLKHGAEP NSADPATSTR

PVHDAAREGF LDTLVVLHRA GARLDARDAW GRTPVDLAEE

LGHRDVARYL RAAAGGTRGS NHARIDAAEG PSDIPD
```

(substituted amino acid residues are shown in bold and underline)

Alignment of amino acid sequences of p16 proteins from sources other than humans, for example, mouse p16 protein (SEQ ID NO: 5) or rat p16 protein (SEQ ID NO: 6) with the amino acid sequence of human p16 protein shows that residues at positions 7, 29, 57, 64, 70, 98 and 105 (corresponding to positions 15, 37, 65, 72, 78, 106, and 113, respectively, on the amino acid sequence of SEQ ID NO: 1) are exposed externally on the three dimensional structure in contact with an aqueous solvent. Of these externally-exposed amino acids, the amino acids at positions 7 (R), 29 (S), 57 (N or S) on the amino acid sequence of SEQ ID NO: 5 or 6 which corresponds, respectively, to tryptophan at position 15(W15), leucine at position 37 (L37), and leucine at position 65 (L65) on the amino acid sequence of the human p16 protein (SEQ ID NO: 1) are not suitable candidates for substitution because they all are hydrophilic. In contrast, the amino acids at positions 64 (C), 70 (F or L), 98 (V) and 105 (L) on the amino acid sequence of SEQ ID NO: 5 or SEQ ID NO: 6, which corresponds, respectively, to cysteine at position 72 (C72), leucine at position 78 (L78), valine at position 106 (V106), and leucine at position 113 (L113) on the amino acid sequence of the human p16 protein (SEQ ID NO: 1) are hydrophobic residues so that at least one of them can be substituted with a hydrophilic amino acid, for example, a negatively or positively charged or polar amino acid, to improve the solubility of the p16 protein.

Another embodiment provides a p16 protein variant comprising a substitution of at least one of amino acids at positions 64, 70, 98, and 105 on the amino acid sequence of SEQ ID NO: 5 or SEQ ID NO: 6, independently with lysine (K), aspartic acid (D), glutamic acid (E), glutamine (Q), asparagine (N), serine (S), alanine (A), threonine (T), or arginine (R). For example, the p16 protein variant may comprise at least one selected from the group consisting of:

a substitution of the amino acid at position 64 on the amino acid sequence of SEQ ID NO: 5 or SEQ ID NO: 6 with serine (S), a substitution of the amino acid at position 70 on the amino acid sequence of SEQ ID NO: 5 or SEQ ID NO: 6 with serine (S), arginine (R), lysine (K), aspartic acid (D), glutamic acid (E), glutamine (Q), or asparagine (N), a substitution of the amino acid at position 98 on the amino acid sequence of SEQ ID NO: 5 or SEQ ID NO: 6 with alanine (A), aspartic acid (D), glutamic acid (E), glutamine (Q), or asparagine (N), and a substitution of the amino acid at position 105 on the amino acid sequence of SEQ ID NO: 5 or SEQ ID NO: 6 with threonine (T), arginine (R), lysine (K), aspartic acid (D), glutamic acid (E), glutamine (Q), asparagine (N), or serine (S).

As described above, cysteine at position 64 (corresponding to C72 of SEQ ID NO: 1) of SEQ ID NO: 5 or SEQ ID NO: 6 may act as a factor to decrease the solubility of the protein by forming an inter-chain disulfide bridge with an adjacent amino acid. Therefore, in an embodiment, the p16 protein variant may comprise a substitution of the amino acid at position 64 on the amino acid sequence of SEQ ID NO: 5 or SEQ ID NO: 6 with serine (S); and optionally further comprise at least one selected from the group consisting of:

a substitution of the amino acid at position 70 on the amino acid sequence of SEQ ID NO: 5 or SEQ ID NO: 6 with serine (S), arginine (R), lysine (K), aspartic acid (D), glutamic acid (E), glutamine (Q), or asparagine (N);

a substitution of the amino acid at position 98 on the amino acid sequence of SEQ ID NO: 5 or SEQ ID NO: 6 with alanine (A), aspartic acid (D), glutamic acid (E), glutamine (Q), or asparagine (N); and a substitution of the amino acid at position 105 on the amino acid sequence of SEQ ID NO: 5 or SEQ ID NO: 6 with threonine (T), arginine (R), lysine (K), aspartic acid (D), glutamic acid (E), glutamine (Q), asparagine (N), or serine (S).

The p16 protein variant may be non-naturally occurring. For example, the p16 protein variant may be synthetic or recombinant.

Another embodiment discloses a polynucleotide encoding a p16 protein variant, a recombinant vector carrying (comprising) the polynucleotide, and a recombinant cell harboring (comprising) the recombinant vector.

The polynucleotide encoding the p16 protein variant may encode the amino acid sequence of SEQ ID NO: 2. For example, the polynucleotide may comprise the nucleotide sequence of SEQ ID NO: 3.

As used herein, the term "vector" refers to a means for expressing a gene of interest in a host cell, as exemplified by a plasmid vector, a cosmid vector, and a viral vector, such as a bacteriophage vector, an adenovirus vector, a retrovirus vector and an adeno-associated virus vector. The recombinant vector may be constructed from well-known plasmids (for example, pSC101, pGV1106, pACYC177, ColE1, pKT230, pME290, pBR322, pUC8/9, pUC6, pBD9, pHC79, pIJ61, pLAFR1, pHV14, pGEX series, pET series, pUC19, etc.), phages (for example, λgt4λB, λ-Charon, λΔz1, M13, etc.) or viruses (for example, SV40, etc.) by known manipulation (genetic engineering) techniques.

In the recombinant vector, the polynucleotide encoding the protein conjugate may be operatively linked to a promoter. The term "operatively linked" is intended to pertain to a functional linkage between a nucleotide sequence of interest and an expression regulatory element (for example, a promoter sequence) so that the expression of the nucleotide sequence of interest is governed by the regulatory element. For instance, when it is "operatively linked" to the regulatory element, the nucleotide sequence of interest can be transcribed and/or translated under the control of the regulatory element.

The recombinant vector may be typically constructed as a cloning vector or an expression vector. For recombinant expression vectors, a vector typically available for expressing a foreign protein in plant, animal or microorganism cells may be employed. Various methods well known in the art may be used for the construction of recombinant vectors.

For use in hosts, such as prokaryotic or eukaryotic cells, the recombinant vector may be constructed appropriately. For example, when a vector is constructed as an expression vector for use in a prokaryotic host, the vector typically includes a strong promoter for transcription (e.g., a pL$^\lambda$ promoter, a CMV promoter, a trp promoter, a lac promoter, a tac promoter, a T7 promoter, etc.), a ribosomal binding side for initiating translation, and transcriptional/translational termination sites. On the other hand, an expression vector for use in a eukaryotic host includes an origin of replication operable in a eukaryotic cell, such as, but not limited to, an f1 origin of replication, an SV40 origin of replication, a pMB1 origin of replication, an adeno origin of replication, an AAV origin of replication, a BBV origin of replication. In addition, the expression vector typically includes a promoter derived from mammalian cells (for example, metallothionein promoter) or from mammalian viruses (for example, adenovirus late promoter, vaccinia virus 7.5K promoter, SV40 promoter, cytomegalovirus promoter and tk promoter of HSV), and a polyadenylation sequence as a transcription termination sequence.

The recombinant cell may be prepared by introducing the recombinant vector into a suitable host cell. So long as it allows for the sequential cloning and expression of the recombinant vector in a stable manner, any host cell known in the art may be employed. Examples of the prokaryotic host cell available may be at least one selected from the group consisting of *E. coli* JM109, *E. coli* BL21, *E. coli* RR1, *E. coli* LE392, *E. coli* B, *E. coli* X 1776, *E. coli* W3110, *Bacillus* spp. such as *Bacillus subtilis* and *Bacillus thuringiensis*, and enterobacteriaceae strains such as *Salmonella typhimurium*, *Serratia marcescens*, and various *Pseudomonas* species. Eukaryotic host cells to be transformed may be at least one selected from the group consisting of *Saccharomyces cerevisiae*, insect cells, plant cells and animal cells including Sp2/0, CHO (Chinese hamster ovary) K1, CHO DG44, PER.C6, W138, BHK, COS-7, 293, HepG2, Huh7, 3T3, RIN, and MDCK, but not be limited thereto.

Using a method well known in the art, the polynucleotide or a recombinant vector carrying the polynucleotide may be introduced (incorporated) into a host cell. This transformation is carried out through CaCl$_2$ or electroporation when the host cell is prokaryotic. For eukaryotic host cells, the genetic introduction may be achieved using, but not limited to, microinjection, calcium phosphate precipitation, electroporation, liposome-mediated transfection, or particle bombardment.

To select a (recombinant vector) transformed host cell, advantage may be taken of the phenotype attributed to a selection marker according to a method known in the art. For example, when the selection marker is a gene resistant to a certain antibiotic, the host cells may be grown in the presence of the antibiotic in a medium to select a transformant of interest.

In the p16 protein variant, the mutated amino acid residues are those that are hydrophobic with external exposure in the three-dimensional conformation of a wild-type p16 protein, and have influence on the solubility of the protein in contact with an aqueous solvent. The p16 protein variant is improved in solubility compared to the wild-type protein because at least one of the externally exposed, hydrophobic residues is substituted by a hydrophilic amino acid, such as an electrically charged amino acid or a polar amino acid. This improvement in protein solubility prevents the p16 protein variant from precipitating upon expression or purification, which leads to increasing the expression of the protein (or the external secretion of the protein). Given an increase in solubility, the p16 protein variant is improved in stability upon formulation and/or storage, and thus can maintain its effective delivery at a high level in vivo upon administration. Additionally, because the amino acid residues which are mutated exist at positions not responsible for binding to Cdk4/6, the p16 protein variant retains affinity for CDKs such as Cdk4/6 at the same level as that of the wild-type p16 and thus functions normally to regulate the cell cycle. In some embodiments, the p16 protein variant is advantageous for mass production thanks to improvement in expression level in host cells, and exhibits such high stability that it can be delivered in an elevated amount in vivo upon administration. In addition, the p16 protein variant retains affinity for CDKs sufficiently to regulate the cell cycle and thus to exert inhibitory activity against cancer by infinite cell division. Hence, the p16 protein variant serves as an effective and potent anticancer agent.

Another embodiment provides a pharmaceutical composition comprising the p16 protein variant as an active ingredient. The pharmaceutical composition is useful for the preventing and/or treating cancer.

Yet another embodiment provides a method of preventing and/or treating cancer, comprising administering the p16 protein variant to a subject in need thereof. The p16 protein variant may be used in a pharmaceutically effective amount, which amount may be determined by the skilled medical practitioner or medical researcher. This method may further comprise identifying the subject is in need of the prevention and/or treatment of cancer, prior to the administration. The step of identifying the subject in need may be conducted by any manner and/or methods known to relevant field for identifying whether or not a subject needs the prevention and/or treatment of cancer. For example, the step of identifying may include diagnosing a subject to have a cancer, or identifying a subject who is diagnosed as a cancer patient.

The pharmaceutical composition may further comprise a pharmaceutical additive, such as a carrier, a diluent and/or an excipient in addition to the p16 protein variant. A pharmaceutically acceptable carrier which is typically used for drug formulations may be available for the pharmaceutical composition. Examples of the carrier include lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate, and mineral oil, but are not limited thereto. In addition, the pharmaceutical composition may further comprise at least one selected from the group consisting of a diluent, an excipient, a lubricant, a humectant, a sweetener, a flavoring agent, an emulsifier, a suspending agent, and a preservative.

The pharmaceutical composition may be administered orally or parenterally. For parenteral administration, the administration may be carried out via intravenous, subcutaneous, intramuscular, intraperitoneal, intradermal, local, intranasal, intrapulmonary, and intrarectal routes, but is not limited thereto. For oral administration, however, the pharmaceutical composition is preferably coated or formulated to protect the active ingredient from being degraded in the stomach because proteins or peptides are digested by pepsin. In addition, the administration may be performed with the aid of an instrument adapted for delivering the pharmaceutical composition to target cells.

A dose of the p16 protein variant in the pharmaceutical composition may vary depending on various factors including the type of formulation; the patient's age, weight, and sex; the severity of the disorder being treated; diet; the time of administration; the route of administration; the rate of excretion; and sensitivity. For example, the pharmaceutically effective amount of the active ingredient in the pharmaceutical composition may range in daily dose from about 0.001 to about 1,000 mg/kg, particularly from about 0.01 to about 100 mg/kg, and more particularly from about 0.1 to about 50 mg/kg, but is not limited thereto. The daily dose may be formulated into a unit dose form or distributed into separate dose forms, or may be included within a multiple dose package. As used herein, the term "pharmaceutically effective amount" refers to an amount at which the active ingredient can exert a desired effect, and may fall within the range set forth above.

The pharmaceutical composition may be formulated into: solutions in oil or aqueous media, suspensions, syrup, emulsions, elixirs, powders, granules, tablets, or capsules, and in this context, a dispersant or a stabilizer may be further employed.

The subject may be intended to encompass all animals that need the delivery of the cytotoxic drug to or into a cancer (tumor) cell, and cells derived (originated or isolated) therefrom. For example, all mammals including primates such as humans and monkeys, and rodents such as mice and rats, cells or tissues derived (originated or isolated) therefrom, and cultures of the cells or tissues may fall into the scope of the subject. The subject may be a person suffering from cancer, or at risk of cancer, or cancer cells or tissues derived (originated or isolated) from the person, a culture thereof; or any combination thereof.

The cancer may be related to the aberrant function of p16. The cancer may be solid cancer or blood cancer. Examples of the cancer include squamous cell carcinoma, small-cell lung cancer, non-small-cell lung cancer, adrenocarcinoma of lung, squamous cell carcinoma of lung, peritoneal cancer, skin cancer, skin or intraocular melanoma, rectal cancer, perianal cancer, esophagus cancer, small intestine cancer, endocrine gland cancer, parathyroid cancer, adrenal cancer, soft-tissue sarcoma, urethral cancer, chronic or acute leukemia, lymphocytic lymphoma, hepatoma, gastric cancer, gastrointestinal cancer, pancreatic cancer, glioblastoma, cervical cancer, ovarian cancer, liver cancer, bladder cancer, hepatocellular adenoma, breast cancer, colon cancer, large intestine cancer, endometrial carcinoma or uterine carcinoma, salivary gland tumor, kidney cancer, prostate cancer, vulvar cancer, thyroid cancer, head or neck cancer, brain cancer, osteosarcoma, or any combination thereof. The cancer may be primary or metastatic cancer.

With regard to the prophylactic and/or therapeutic effect on cancer, the composition suppresses cancer cells from undergoing migration, invasion and/or metastasis, in addition to inhibiting the growth of primary cancer cells. Therefore, the composition not only inhibits cancer cell growth, but also suppresses the malignancy of cancer due to migration, invasion and metastasis.

Another embodiment provides a method of preparing a p16 protein variant having increased solubility or a method of increasing solubility of p16 protein, comprising mutating (e.g., substituting) at least one of hydrophobic amino acid residues externally exposed on a three-dimensional structure of p16 with a different amino acid.

As described above, a hydrophobic amino acid residue exposed externally on the 3-dimensional structure of p16 may be in contact with an aqueous solvent and located at a position that is not involved in the binding of CDKs (e.g., Cdk4/6). The hydrophobic amino acid residue may be at least one selected from the group consisting of tryptophan at position 15 (W15), leucine at position 37 (L37), leucine at position 65 (L65), cysteine at position 72 (C72), leucine at position 78 (L78), valine at position 106 (V106), and leucine at position 113 (L113), or any combination thereof; on the amino acid sequence of SEQ ID NO: 1, or at least one selected from the group consisting of amino acids at positions 64, 70, 98, and 105, or any combination thereof; on the amino acid sequence of SEQ ID NO: 5 or SEQ ID NO: 6.

The mutation may be substitution of at least one of the amino acid residues with a different amino acid. For example, the mutation may be a substitution of at least one selected from the group consisting of tryptophan at position 15(W15), leucine at position 37 (L37), leucine at position 65 (L65), cysteine at position 72 (C72), leucine at position 78 (L78), valine at position 106 (V106), and leucine at position 113 (L113) on the amino acid sequence of SEQ ID NO: 1, independently with lysine (K), aspartic acid (D), glutamic acid (E), glutamine (Q), asparagine (N), serine (S), alanine (A), threonine (T), or arginine (R). In detail, the mutation may comprise a substitution of at least one selected from the group consisting of tryptophan at position 15(W15), leucine at position 65 (L65), cysteine at position 72 (C72), and leucine at position 113 (L113) independently with lysine (K), aspartic acid (D), glutamic acid (E), glutamine (Q), asparagine (N), serine (S), alanine (A), threonine (T), or arginine (R) (in this regard, the mutation of cysteine at position 72 (C72) may be obligatory) alone; or in combination with a substitution of at least one selected from the group consisting of: leucine at position 37 (L37), leucine at position 78 (L78), and valine at position 106 (V106) independently with lysine (K), aspartic acid (D), glutamic acid (E), glutamine (Q), asparagine (N), serine (S), alanine (A), threonine (T), or arginine (R).

The method of preparing the p16 protein variant can comprise providing a polypeptide having the amino acid sequence described above (e.g., SEQ ID NO: 1, 5, or 6 having the described substitutions). The polypeptide can be provided by any suitable method, such as by expressing a polynucleotide encoding the polypeptide in a cell, whereby the polypeptide is produced. Alternatively, the polypeptide may be synthesized using well-known protein synthesis techniques.

The method for preparing a p16 protein variant having increased solubility or increasing solubility of p16 protein may comprise carrying out at least one substitution of a p16 protein selected from the group consisting of:

substitution of tryptophan at position 15 (W15) on the amino acid sequence of SEQ ID NO: 1 with lysine (K), arginine (R), aspartic acid (D), glutamic acid (E), glutamine (Q), asparagine (N), or serine (S), substitution of leucine at position 37 (L37) on the amino acid sequence of SEQ ID NO: 1 with aspartic acid (D), arginine (R), lysine (K), glutamic acid (E), glutamine (Q), serine (S), or asparagine (N), substitution of leucine at position 65 (L65) on the amino acid sequence of SEQ ID NO: 1 with lysine (K), arginine (R), aspartic acid (D), glutamic acid (E), glutamine (Q), asparagine (N), or serine (S), substitution of cysteine at position 72 (C72) on the amino acid sequence of SEQ ID NO: 1 with serine (S), substitution of leucine at position 78 (L78) on the amino acid sequence of SEQ ID NO: 1 with serine (S), arginine (R), lysine (K), aspartic acid (D), glutamic acid (E), glutamine (Q), or asparagine (N), substitution of valine at position 106 (V106) on the amino acid sequence of SEQ ID NO: 1 with alanine (A), aspartic acid (D), glutamic acid (E), glutamine (Q), or asparagine (N), and substitution of leucine at position 113 (L113) on the amino acid sequence of SEQ ID NO: 1 with threonine (T), arginine (R), lysine (K), aspartic acid (D), glutamic acid (E), glutamine (Q), asparagine (N), or serine (S).

In one embodiment, the method for preparing a p16 protein variant having increased solubility or for increasing solubility of p16 protein may comprise carrying out a substitution of cysteine at position 72 (C72) of SEQ ID NO: 1 with serine (S).

In another embodiment, the method for preparing a p16 protein variant having increased solubility or for increasing solubility of p16 protein may further comprise, in addition to the substitution of C72, carrying out at least one substitution of an amino acid of SEQ ID NO: 1 selected from the group consisting of:

a substitution of tryptophan at position 15 (W15) with lysine (K), arginine (R), aspartic acid (D), glutamic acid (E), glutamine (Q), asparagine (N), or serine (S), a substitution of leucine at position 65 (L65) with lysine (K), arginine (R), aspartic acid (D), glutamic acid (E), glutamine (Q), asparagine (N), or serine (S), and a substitution of leucine at position 113 (L113) with threonine (T), arginine (R), lysine (K), aspartic acid (D), glutamic acid (E), glutamine (Q), asparagine (N), or serine (S).

In another embodiment, the method for preparing a p16 protein variant having increased solubility or for increasing solubility of p16 protein may further comprise, in addition to the substitution of C72 and at least one substitution of an amino acid of SEQ ID NO: 1 selected from among W15, L65, and L113, carrying out at least one substitution selected from the group consisting of a substitution of leucine at position 37 (L37) with aspartic acid (D), arginine (R), lysine (K), glutamic acid (E), glutamine (Q), serine (S), or asparagine (N), a substitution of leucine at position 78 (L78) with serine (S), arginine (R), lysine (K), aspartic acid (D), glutamic acid (E), glutamine (Q), or asparagine (N), and a substitution of valine at position 106 (V106) with alanine (A), aspartic acid (D), glutamic acid (E), glutamine (Q), or asparagine (N).

In another embodiment, the method of preparing a p16 protein variant having increased solubility or a method of increasing solubility of p16 protein may comprise substituting at least one selected from amino acids at positions 64, 70 and 105 on the amino acid sequence of SEQ ID NO: 5 or SEQ ID NO: 6 independently with lysine (K), aspartic acid (D), glutamic acid (E), glutamine (Q), asparagine (N), serine (S), alanine (A), threonine (T), or arginine (R).

The amino acid substitutions can be made using routine techniques, such as by mutating or otherwise preparing a polynucleotide sequence that encodes an amino acid sequence comprising the foregoing mutations.

The amino acids to be mutated according to one embodiment are hydrophobic with exposure to an aqueous external environment on the three-dimensional structure of p16 protein, and are located at positions not responsible for binding to CDKs (e.g., Cdk4/6). The hydrophobic amino acid residues exposed externally on the three-dimensional structure may be selected as suitable for amino acid substitution by comparing amino acid sequences, and/or secondary and/or tertiary structures between a p16 protein and proteins with ankyrin repeat (ANK) motif, wherein the ANK repeat motif not only exhibits a high expression level in host cells, such as *E. coli*, but also are highly soluble and similar in secondary or tertiary structure to p16 protein. For example, the proteins with ANK repeat motif which not only exhibit a high expression level in host cells, such as *E. coli*, but also are highly soluble and similar in secondary or tertiary structure to p16 protein may be selected from the group consisting of designed ankyrin repeat proteins (i.e., DARPins, examples of which include PDB 3HGO; SEQ ID NO: 7). For example, the comparison of a secondary structure-based alignment of human p16 protein (SEQ ID NO: 1) with the DARPin PDB 3HGO is shown in FIG. 7 wherein positions at which the amino acids are externally exposed and not responsible for binding to Cdk4/6 are indicated by ▼ or ●.

Alignment of secondary or tertiary structure-based amino acid sequences between a protein of interest to be improved in solubility and a reference protein that is of high solubility having similarity in secondary or tertiary structure to the protein of interest allows a person skilled in the art to locate (i.e., search for) positions (e.g., hydrophobic residues) at which desirable mutations would be achieved, to increase the solubility (e.g., solubility is an aqueous solution) of the protein of interest (with the proviso that the amino acids are hydrophobic residues exposed to an aqueous solvent and are not responsible for the original function of the protein of interest). Substituting the hydrophobic amino acids at these positions with hydrophilic residues could increase the solubility of the protein of interest.

Another embodiment provides a method of analyzing secondary or tertiary structure of a protein of interest, and a method of providing information for increasing the solubility of a protein of interest or a method of increasing the solubility of a protein of interest using the method of analyzing secondary or tertiary structure of a protein of interest described above.

The method of analyzing secondary or tertiary structure of a protein of interest may comprise conducting secondary or tertiary structure-based amino acid sequence alignment between the protein of interest (e.g., p16) and a reference protein (e.g., a DARPin). The term "secondary or tertiary structure-based amino acid sequence alignment" may refer to comparison of amino acid sequences aligned on a secondary or tertiary structure between a protein of interest and a reference protein.

Any protein that is to be analyzed for its structure may be the protein of interest. For example, any biological protein that is to be conferred with increased solubility, with the aim of improving its formulation stability and in vivo delivery efficiency may be the protein of interest. The protein of interest may be at least one anticancer protein selected from the group consisting of, but not limited to, INK4 lineage proteins (for example, p15 (INK4b; e.g., human p15 protein (Accession No. P42772), mouse p15 protein (Accession No. P55271), rat p15 protein (Accession No. P55272), etc.), p16 (INK4a; e.g., human p16 protein (Accession No. NP_000068; SEQ ID NO: 1), mouse p16 protein (Accession No. NP_001035744; SEQ ID NO: 5), rat p16 protein (SEQ ID NO: 6), etc.), p18 (INK4c; e.g., human p18 protein (Accession No. NP_001253), mouse p18 protein (Accession No. NP_031697), etc.), p19 (INK4d; e.g., human p19 protein (Accession No. NP 001791), mouse p19 protein (Accession No. NP_034008)), etc.), p53 (e.g., human p53 protein (Accession No. NP_000537), and mouse p53 protein (Accession No. NP_001120705, etc.), or any combination thereof.

The reference protein may be highly soluble and have a secondary or tertiary structure similar to that of a protein of interest. For ease in acquirement, the reference protein may be one expressed at a high efficiency in a host cell, such as *E. coli*. For example, the reference protein may be a protein with ANK repeat(s), for example, a DARPin.

DARPins are genetically engineered antibody mimetic proteins which exhibit high specificity and high binding-affinity to target protein. They are derived from natural ankyrin proteins and consist of at least two, usually three, four or five repeat motifs of these proteins. Their molecular mass is about 10, 14 or 18 kDa for three-, four- or five-repeat DARPins, respectively.

In one embodiment, a DARPin available for use as the reference protein may be selected from the group consisting of DARPins containing 4 ANK repeats (e.g., DARPin 3HGO, 2Y0B, 2XZT, 2XZD, 2V4H), DARPins containing 5-ANK repeats (e.g., DARPin 2Y1L, 2J8S, 4DX6, 5V5Q, 4DRX, 2P2C, 3NOG), and a combination thereof Amino acid sequences of the DARPins available for use as reference proteins are given in Tables 1 and 2, below:

TABLE 1

DARPin containing 4 ANK repeats

| DARPin | Amino acid sequence |
|---|---|
| 3HGO | MRGSHHHHHHGSDLGKKLLEAARAGQDDEVRILMANGADVNAEDKVGLTPLHLAAMNDH<br>LEIVEVLLKNGADVNAIDAIGETPLHLVAMYGHLEIVEVLLKHGADVNAQDKFGKTAFDISID<br>NGNEDLAEILQKLN (SEQ ID NO: 7) |
| 2Y0B | MRGSHHHHHHGSDLGKKLLEATRAGQDDEVRILMANGADVNAMDDAGVTPLHLAAKRGH<br>LEIVEVLLKHGADVNARDIWGRTPLHLAATVGHLEIVEVLLEYGADVNAQDKFGKTAFDISID<br>NGNEDLAEILQKLN (SEQ ID NO: 8) |

TABLE 1-continued

DARPin containing 4 ANK repeats

DARPin Amino acid sequence

2XZT  <u>MRGSHHHHHH</u>GSDLGKKLLEATRAGQDDEVRILMANGADVNAMDDAGVTPLHLAAKRGH
LEIVEVLLKHGADVNASDSWGRTPLHLAATVGHLEIVEVLLEYGADVNAQDKFGKTAFDISID
NGNEDLAEILQKLN (SEQ ID NO: 9)

2XZD  <u>MRGSHHHHHH</u>GSDLGKKLLEATRAGQDDEVRILMANGADVNAMDDAGVTPLHLAAKRGH
LEIVEVLLKHGADVNASDIWGRTPLHLAATVGHLEIVEVLLEYGADVNAQDKFGKTAFDISID
NGNEDLAEILQKLN (SEQ ID NO: 10)

2V4H  <u>HHHHHHHHHH</u>GSDLGKKLLEAARAGQDDEVRILMANGADVNANDRKGNTPLHLAADYDH
LEIVEVLLKHGADVNAHDNDGSTPLHLAALFGHLEIVEVLLKHGADVNAQDKFGKTAFDISID
NGNEDLAEILQKLN (SEQ ID NO: 11)

TABLE 2

DARPin containing 5 ANK repeats

DARPin Amino acid sequence

2Y1L  <u>MRGSHHHHHH</u>GSDLGKKLLEAARAGRDDEVRILMANGADVNAEDASGWTPLHLAAFNGHLEI
VEVLLKNGADVNAVDHAGMTPLRLAALFGHLEIVEVLLKNGADVNANDMEGHTPLHLAAMFG
HLEIVEVLLKNGADVNAQDKFGKTAFDISIDNGNEDLAEILQKLN (SEQ ID NO: 12)

2J8S  <u>MRGSHHHHHH</u>GSDLGKKLLEAARAGRDDEVRILMANGADVNAADVVGWTPLHLAAYWGHL
EIVEVLLKNGADVNAYDTLGSTPLHLAAHFGHLEIVEVLLKNGADVNAKDDNGITPLHLAANRG
HLEIVEVLLKYGADVNAQDKFGKTAFDISINNGNEDLAEILQKLN (SEQ ID NO: 13)

4DX6  <u>MRGSHHHHHH</u>GSDLGKKLLEAARAGRDDEVRILMANGADVNAADVVGWTPLHLAAYWGHL
EIVEVLLKNGADVNAYDTLGSTPLHLAAHFGHLEIVEVLLKNGADVNAKDDNGITPLHLAANRG
HLEIVEVLLKYGADVNAQDKFGKTAFDISINNGNEDLAEILQKLN (SEQ ID NO: 14)

4DRX  <u>MRGSHHHHHH</u>GSDLGKKLLEAARAGQDDEVRILMANGADVNATDASGLTPLHLAATYGHLEI
VEVLLKHGADVNAIDIMGSTPLHLAALIGHLEIVEVLLKHGADVNAVDTWGDTPLHLAAIMGHL
EIVEVLLKHGADVNAQDKFGKTAFDISIDNGNEDLAEILQKLN (SEQ ID NO: 15)

2P2C  <u>MRGSHHHHHH</u>GSDLGKKLLEAARAGQDDEVRILMANGADVNATDWLGHTPLHLAAKTGHLEI
VEVLLKYGADVNAWDNYGATPLHLAADNGHLEIVEVLLKHGADVNAKDYEGFTPLHLAAYDG
HLEIVEVLLKYGADVNAQDKFGKTAFDISIDNGNEDLAEILQKLN (SEQ ID NO: 16)

3NOG  <u>MRGSHHHHHH</u>GSDLGKKLLEAARAGQDDEVRILMANGADVNASDHVGWTPLHLAAYFGHLEI
VEVLLKNGADVNADDSLGVTPLHLAADRGHLEVVEVLLKNGADVNANDHNGFTPLHLAANIG
HLEIVEVLLKHGADVNAQDKFGKTAFDISIDNGNEDLAEILQKLN (SEQ ID NO: 17)

(In Tables 1 and 2, the underlined regions of the amino acid sequences represent an N-terminal His tag for purification, and may be omitted/removed from the final purified proteins)

Considering structural similarity, the reference protein may be a DARPin containing 4 ANK repeats (e.g., DARPin 3HGO, 2Y0B, 2XZT, 2XZD, 2V4H, etc.) when the protein of interest is p15 or p16, and a DARPin containing 5 ANK repeats (e.g., DARPin 2Y1L, 2J8S, 4DX6, 5V5Q, 4DRX, 2P2C, 3NOG, etc.) when the protein of interest is p18 or p19.

The method for providing information for a protein of interest in solubility or a method for increasing a protein of interest in solubility may be based on the method for analyzing the protein of interest for secondary or tertiary structure. The information providing method may contribute to an increase in the solubility of the protein of interest by providing information on positions at which mutations relevant to solubility might be performed.

In another embodiment, a method of providing information for increasing solubility of a protein of interest or a method of increasing solubility of a protein of interest may comprise:

comparing solvent-exposed (e.g., aqueous solvent-exposed) regions between the protein of interest and a reference protein through secondary or tertiary structure-based amino acid sequence alignment; and searching for and identifying a position (amino acid) of the solvent exposed region of the protein of interest where the protein of interest has a hydrophobic amino acid while the reference protein has a hydrophilic amino acid at the corresponding position of the solvent exposed region of the reference protein.

The protein of interest and the reference protein available for the method are as described above.

In another embodiment, the method for providing information for increasing a protein of interest in solubility or a method for increasing a protein of interest in solubility may further comprise selecting the reference protein prior to the comparison of solvent-exposed (e.g., aqueous solvent-exposed) regions between the two proteins (protein of interest/reference protein).

In addition, the method for providing information for increasing a protein of interest in solubility or a method for increasing a protein of interest in solubility may further comprise preparing information on the secondary or tertiary structures of both the protein of interest and the reference protein prior to the comparison of solvent-exposed regions between the two proteins (and/or subsequent to the selection of the reference protein). Information on the secondary or tertiary structures of proteins of interest and reference proteins may be found in various databases or obtained using a protein structure (sequence) analysis tool (such as a general device and/or software). The database and/or the analysis tool available for preparing information on the secondary or tertiary structures of proteins are well known in the art. For example, information from Phyre2 (Imperial College of London, Structural Bioinformatics Group, available online at <<www.sbg.bio.ic.ac.uk/phyre2/>>), and/or DALI database (available online at <<ekhidna.biocenter.helsinki.fi/dali_server/>>) may be searched for, using a typical protein structure (sequence) analysis tool (e.g., ClustalW2 tool (available online at <<www.ebi.ac.uk/Tools/msa/clustalw2/>>) for secondary alignment, Coot program (available online at <<www.ysbl.york.ac.uk/~lohkamp/coot/wincoot-download.html>>) for tertiary structure-based alignment and the like).

For use in the comparison step, the solvent-exposed regions of proteins of interest and reference proteins may be determined with reference to information on the secondary or tertiary structures of the proteins.

If an amino acid at a position of the solvent exposed region of the protein of interest is hydrophobic while an amino acid at the corresponding position of the solvent exposed region of the reference protein is hydrophilic, the hydrophobic amino acid of the protein of interest may be a candidate for mutation (substitution). Its substitution with a hydrophobic amino acid may increase the solubility of the protein of interest.

Therefore, the method of increasing solubility of the protein of interest may further comprise substituting the selected hydrophobic amino acid of the protein of interest with a hydrophilic amino acid, subsequent to the searching/identifying step. In one embodiment, the method for increasing solubility of a protein of interest comprises:

comparing solvent-exposed regions of the protein of interest and a reference protein through secondary or tertiary structure-based alignment therebetween;

searching for a position of the solvent exposed region of the protein of interest where the protein of interest has a hydrophobic amino acid while the reference protein has a hydrophilic amino acid at the corresponding position of the solvent exposed region of the reference protein; and substituting the hydrophobic amino acid at the position in the protein of interest with a hydrophilic amino acid.

The hydrophobic amino acid to be substituted may be selected from the group consisting of leucine, cysteine, valine, phenyl alanine (F), tryptophan (W), isoleucine (I), proline (P), methionine (M), and a combination thereof. As a substituent, the hydrophilic amino acid may be selected from the group consisting of lysine (K), aspartic acid (D), glutamic acid (E), glutamine (Q), asparagine (N), serine (S), alanine (A), threonine (T), arginine (R), and a combination thereof. One or more hydrophobic amino acids may be candidates for mutation and may be independently substituted with the same or different hydrophilic amino acids. In addition, selection may be made of a hydrophobic amino acid in consideration of the size (e.g., volume and/or molecular weight) of the originally positioned hydrophobic amino acid to be substituted in order to prevent a significant (substantial) change in the secondary or tertiary structure of the protein of interest or a negative effect on the original function of the protein of interest after mutation (substitution), which can be determined by a person skilled in the relevant art. A mutation without a significant (substantial) change in the secondary or tertiary structure (or original function) of a wild-type protein is not difficult for a person having ordinary skill in the art.

For example, the suitable hydrophilic amino acids substitutable for each hydrophobic amino acid without substantial change in the secondary or tertiary structure of the protein of interest or a negative effect on the original function of the protein of interest, are summarized in the following table:

| Hydrophobic amino acid | Suitable hydrophilic amino acid |
|---|---|
| Leucine (L) | aspartic acid (D), arginine (R), lysine (K), glutamic acid (E), glutamine (Q), serine (S), asparagine (N), or threonine (T) |
| Cysteine (C) | serine (S) |
| Valine (V) | alanine (A), aspartic acid (D), glutamic acid (E), glutamine (Q), or asparagine (N) |
| Phenyl alanine (F) | Tyrosine (Y), Histidine (H) |
| Tryptophan (W) | lysine (K), arginine (R), aspartic acid (D), glutamic acid (E), glutamine (Q), asparagine (N), or serine (S) |
| Isoleucine (I) | aspartic acid (D), glutamic acid (E), glutamine (Q), serine (S), asparagine (N), or threonine (T) |
| Methionine (M) | aspartic acid (D), glutamic acid (E), glutamine (Q), serine (S), asparagine (N), or threonine (T) |

The mutation candidates are hydrophobic amino acids, and their positions may fall within the solvent-exposed regions and not affecting a site responsible for the inherent function of the protein, for example, an active site of the protein of interest or an interaction (binding) site between the protein of interest and its target.

As it is greatly improved in solubility, the p16 protein variant can be formulated to a stable form, with the concomitant retention of affinity for Cdk4/6. Thus, it can be usefully applied to the treatment of cancer. When the p16 protein variant is fused with a cell membrane penetration peptide, it can be encouraged to exhibit more potent anticancer activity.

EXAMPLES

Hereafter, the present invention will be described in detail by examples.

The following examples are intended merely to illustrate the invention and are not construed to restrict the invention.

Example 1

Determination of Mutation Position of p16 Protein

The positions at which hydrophobic amino acids located with external exposure on the three dimensional structure of p16 protein were to be substituted by hydrophilic amino acids were determined in the following experiments.

Figure 2:
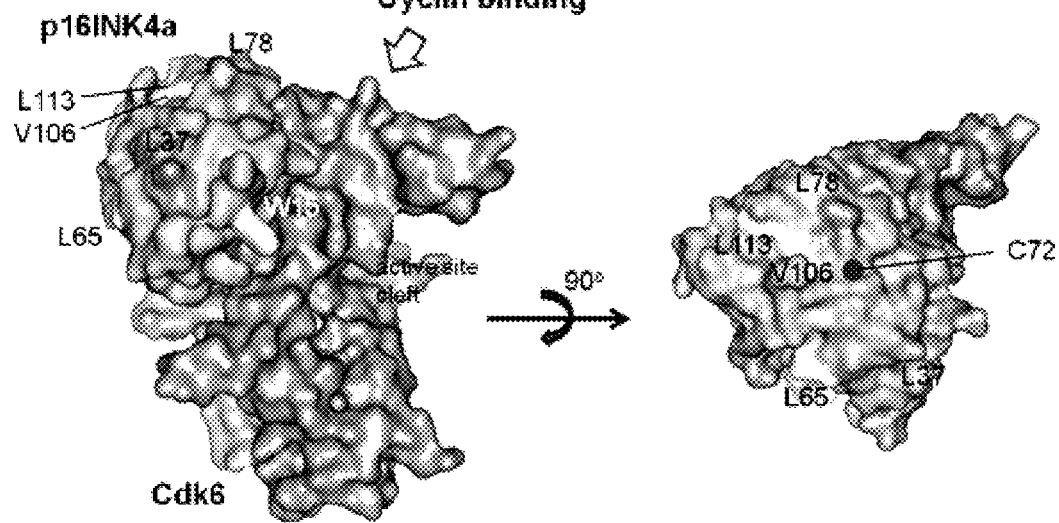
FIG. 2 is a schematic illustrating mutation points on the human p16 protein, as analyzed by three-dimensional structure modeling.

With the aid of Phyre2 (<<www.sbg.bio.ic.ac.uk/phyre2/>>) the human p16 protein (SEQ ID NO: 1) was analyzed for secondary structure (see FIG. 7), and its three-dimensional structure was modeled (see FIG. 2).

A DALI database (<<ekhidna.biocenter.helsinki.fi/dali_server>>) search identified that a DARPin containing 3 ANK repeats (PDB 3HGO) (SEQ ID NO: 7) is the most similar in three dimensional structure to human p16 protein, and is expressed in E. coli, with an increased solubility. Based on this result, the DARPin (PDB 3HGO) (SEQ ID NO: 7) was employed as a template to determine the mutation points of the p16 protein.

Figure 8:
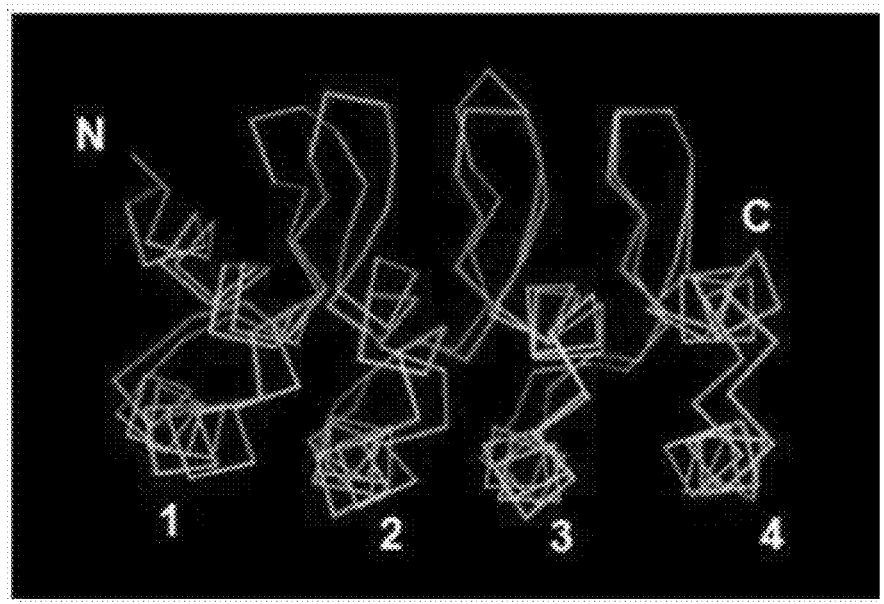
FIG. 8 illustrates the superimposition of the human p16 protein (SEQ ID NO: 1) on a DARPin (PDB 3HGO; SEQ ID NO: 7)

The LSQKAB program in CCP4 module (ftp://ftp.ccp4.ac.uk/ccp4/4.0.1/ccp4-4.0.1/ccp4i/help/modules/coord_utils.html) (least-square method) was used for secondary and tertiary structural superposition between human p16 protein (SEQ ID NO: 1) and DARPin 3HGO (SEQ ID NO: 7) to identify their similarity, and the results are given in FIG. 8.

On the basis of the secondary (mainly α-helix) or tertiary structures obtained above, amino acid sequence alignment between human p16 protein (SEQ ID NO: 1) and DARPin 3HGO (SEQ ID NO: 7) was performed, and the results are given in FIGS. 2 and 7. Like this, mutation points of human p16 were determined by secondary or tertiary structure analysis. Human p16 variants in which hydrophobic amino acids were substituted at the mutation points were designed. The mutation points and the substituted amino acids at the mutation points are given in Table 3, below:

TABLE 3

|   | p16INK4a | DAR(3HG0) | Mutation |
|---|----------|-----------|----------|
| 1 | W15 | K | K |
| 2 | L37 | D | D |
| 3 | L65 | K | K |
| 4 | C72 | A | S |
| 5 | L78 | G | S |
| 6 | V106 | A | A |
| 7 | L113 | T | T |

Example 2

Preparation of Strain Expressing p16 Protein Variant

Human p16 protein (wild-type) (SEQ ID NO: 1), and a p16 protein variant (SEQ ID NO: 2) in which substitution of tryptophan at position 15 (W15) with lysine (K), leucine at position 37 (L37) with aspartic acid (D), leucine at position 65 (L65) with lysine (K), cysteine at position 72 (C72) with serine (S), leucine at position 78 (L78) with serine (S), valine at position 106 (V106) with alanine (A), and leucine at position 113 (L113) with threonine (T) were prepared.

To prepare the human p16 protein (wild-type) of SEQ ID NO: 1 and the p16 protein variant of SEQ ID NO: 2, polynucleotides encoding them (human p16 protein: NM_000077.4 (SEQ ID NO: 4); human p16 protein variant: SEQ ID NO: 3) were used. In detail, the polynucleotides were cloned to pET21b vector (Novagen) using the restriction enzymes NdeI (NEB) and XhoI (NEB) to construct recombinant vectors pET21b:WT p16INK4a, and pET21b:p16INK4a variant which were configured to express human p16 protein (wild-type) and human p16 protein variant, respectively. These recombinant vectors were introduced into an E. coli strain (BL21(DE3)Codon Plus-RIPL; Invitrogen) to afford recombinant strains pET21b:WT p16INK4a/BL21(DE3)CodonPlus-RIPL and pET21b:p16INK4a variant/BL21(DE3)Codon Plus-RIPL which aimed to express the human p16 protein (wild-type) and the human p16 protein variant, respectively.

Likewise, polynucleotides (SEQ ID NOS: 3 and 4) coding respectively for the p16 protein variant of SEQ ID NO: 1 and the human p16 protein (wild-type) of SEQ ID NO: 1 were cloned to pGEX-4T3 using the restriction enzymes BamHI (NEB) and XhoI (NEB) (Novagen) to construct recombinant expression vectors pGEX-4T3:p16INK4a variant and pGEX-4T3:WT p16INK4a which were then transformed to E. coli strain (BL21(DE3)Codon Plus-RIPL; Invitrogen) to afford recombinant strains pGEX-4T3:p16INK4a variant/BL21(DE3)Codon Plus-RIPL for expressing the human p16 protein variant, and pGEX-4T3:WT p16INK4a/BL21(DE3) CodonPlus-RIPL for expressing the human p16 protein.

Example 3

Solubility of p16 Protein Variant

A primary culture of each of the recombinant strains prepared in Example 2, pET21b:WT p16INK4a/BL21(DE3) CodonPlus-RIPL and pET21b:p16INK4a variant/BL21(DE3)Codon Plus-RIP was inoculated in an amount of 100 µL to 5 mL of LB broth (Sigma; Tryptone (pancreatic digest of casein) 10 g/L, Yeast extract 5 g/L, NaCl 5 g/L), and incubated O/N (overnight) at 37° C. When OD600 reached ~0.8, culturing was continued at 18° C. for 12 hrs in the presence of 1 mM IPTG (Isopropyl-β-D-thio-galactoside).

5 mL of the culture was centrifuged at 4° C. and 4000 rpm for 10 min. The cell pellet was resuspended in 0.4 mL of a lysis buffer (1×PBS pH 7.4), followed by sonication (pulse 1 s/1 s, 50% amplitude, 1 min) to lyse the cells. 20 µL was sampled from the cell lysate (total sample: total). After centrifugation of the cell lysate at 4° C. and 13200 rpm for 10 min, 20 µL was sampled from the supernatant (supernatant sample: sup). Separately, the inclusion body (IB) precipitate was resuspended in 0.4 mL of 1×PBS pH 7.4, and 20 µL was sampled from the suspension (inclusion body sample). Each sample was boiled at 95° C. for 5 min and then subjected to SDS-PAGE.

Figure 3:
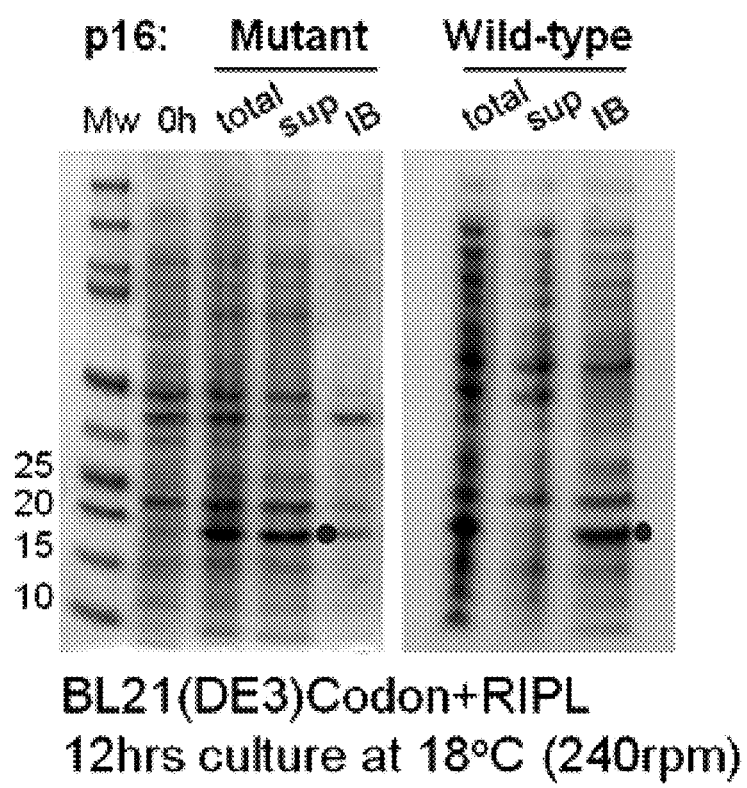
FIG. 3 is an image of a gel electrophoresis displaying the expression patterns of the wild-type p16 and the p16 variant according to one embodiment in total cell lysates (Total), supernatants (sup), and inclusion bodies (IB).

The results are shown in FIG. 3. As can be seen in FIG. 3, most of the wild-type p16 protein (almost 100%) was detected in the inclusion body, whereas most of the p16 protein variant (more than 90%) was detected in the supernatant, indicating that almost all of the wild-type p16 protein was expressed in an insoluble form in the E. coli strain whereas more than 90% of the p16 protein variant was expressed as a soluble entity. The soluble protein was extracellularly secreted through the cell membrane, as demonstrated by an increase in the extracellular amount of the protein (molecular weight of p16 and p16 variant: 16 kDa).

Example 4

Purification of p16 Protein Variant

A suspension of 2 mL of pET21b:p16INK4a variant/BL21(DE3)Codon Plus-RIPL (primary culture), prepared in Example 2, in 1 L of LB broth (Sigma; Tryptone (pancreatic digest of casein) 10 g/L, Yeast extract 5 g/L, NaCl 5 g/L) was incubated ON (overnight) at 37° C.

When OD600 reached ~0.8, 1 mM IPTG (Isopropyl-β-D-thio-galactoside) was added to the culture before incubation at 18° C. for an additional 12 hrs. The cell culture (1 L) was centrifuged at 4° C. and 4000 rpm for 10 min, and the cell pellet was resuspended in 50 mL of a lysis buffer (20 mM Tris-HCl pH8.0, 1 mM PMSF), followed by sonication (pulse 1 s/1 s, 50% amplitude, 1 min, 4 times total). After centrifugation of the resulting cell lysate at 4° C. and 18000 rpm for 50 min, the supernatant was purified by ion-exchange chromatography using an AKTA FPLC system (GE Healthcare). The following column and buffer were used:

Column: HiTrap Q, 5 mL size, GE Healthcare,
Buffer: A=20 mM Tris-HCl pH 8.0, B=20 mM Tris-HCl pH 8.0, 1 M NaCl.

The p16 protein variant was eluted using a linear gradient (0→1 M NaCl, 100 mL length). The eluate was subjected to size-exclusion chromatography (SEC) using the following column and buffer:

Column: 10/300 superdex-75 gl (GE Healthcare)
Buffer: 1×PBS pH 7.4

The p16 protein variant fraction obtained by SEC was purified to a final concentration of 5 mg/mL (3 mM) by ultrafiltration using YM-10 filter (Millipore).

Figure 4:
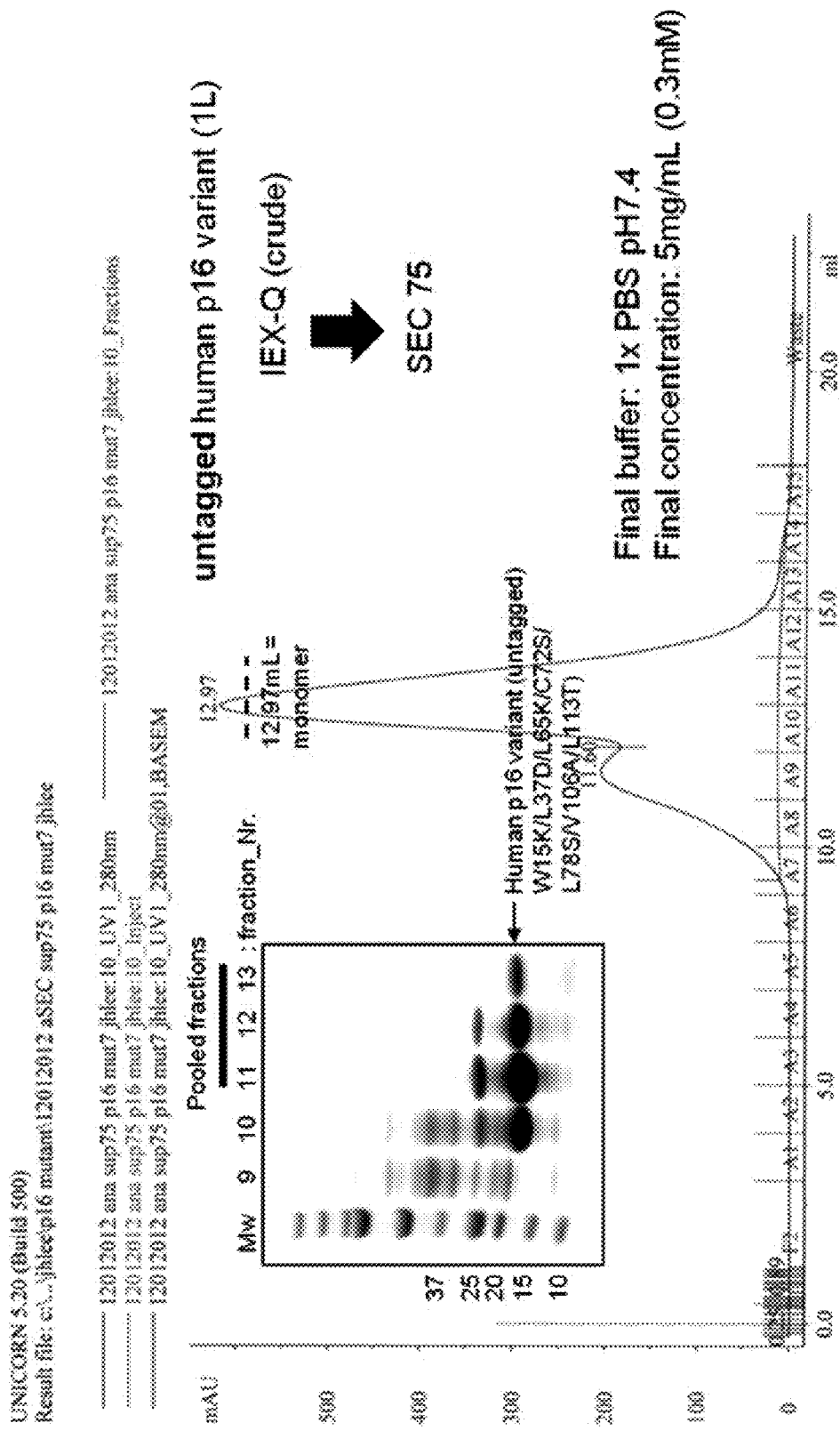
FIG. 4 shows the result of the size-exclusion chromatography of a p16 variant.

The purification result is illustrated in FIG. 4. As shown in FIG. 4, the purified p16 protein variant was homogeneous in size as measured by size-exclusion chromatography, and could be concentrated to more than 0.3 mM.

Example 5

Assay for Binding of p16 Protein Variant to Cdk4/6

To 5 mL of LB broth (Sigma; Tryptone (pancreatic digest of casein) 10 g/L, Yeast extract 5 g/L, NaCl 5 g/L) was inoculated 100 μL of the pGEX-4T3:p16INK4a variant/BL21(DE3)Codon Plus-RIPL (primary culture) prepared in Example 2, followed by incubation O/N (overnight) at 37° C. The p16 protein variant was purified from the culture in the same manner as in Example 3, and used in an assay for binding to Cdk4/6, as follows.

A Cdk6 (Abcam's ab84717, recombinant full length Human Cdk6 (amino acids 1-326) with N-terminal His tag) was diluted to 1 μg/ml in a bicarbonate/carbonate buffer (100 mM, pH 9.6; 3.03 g $Na_2CO_3$, 6.0 g $NaHCO_3$, in 1000 ml distilled water), and 50 μL of the dilution was aliquoted to each well of 96-well plates (Nun's MaxiSorp) for ELISA and incubated overnight at 4° C. After aspiration of the Cdk6 solution therefrom, each well of the plates was washed twice with 200 μL of PBST (PBS+Tween 20: 1.16 g $Na_2HPO_4$, 0.1 g KCl, 0.1 g $K_3PO_4$, 4.0 g NaCl (in 500 ml distilled water), pH 7.4; 0.05% (v/v) Tween 20). Then, each well thus coated with Cdk6 was incubated with 200 μL of a blocking solution (5% (v/v) skim milk in PBST) at room temperature for 1 hr, followed by two rounds of washing with PBST 200 μL of PBST.

To each well coated with the Cdk6 protein, 100 μL of the p16 protein variant purified at various concentrations (0, 0.001, 0.01, 0.1, 1, and 10 μM) in Example 3 was added. After 2 hours of incubation at room temperature, unreacted proteins were removed, and each well was washed twice with 200 μL of PBST.

Each well was added with 100 μL of a 1/200 dilution of the anti-p16 antibody (Abcam's ab6546; primary antibody) in a blocking solution (5%(v/v) skim milk in PBST) and incubated at room temperature for 1 hr. After removal of the antibody solution, each well was washed twice with 200 μL of PBST.

A 1/2500 dilution of an anti-rabbit IgG antibody (HRP) (Thermo's SA1-9510; secondary antibody) in a blocking solution was added in an amount of 100 μL to each well, and incubated at room temperature for 30 min. Thereafter, after removal of the antibody solution, each well washed four times with 200 μL of PBST and then twice with 200 μL of PBS.

Figure 5:
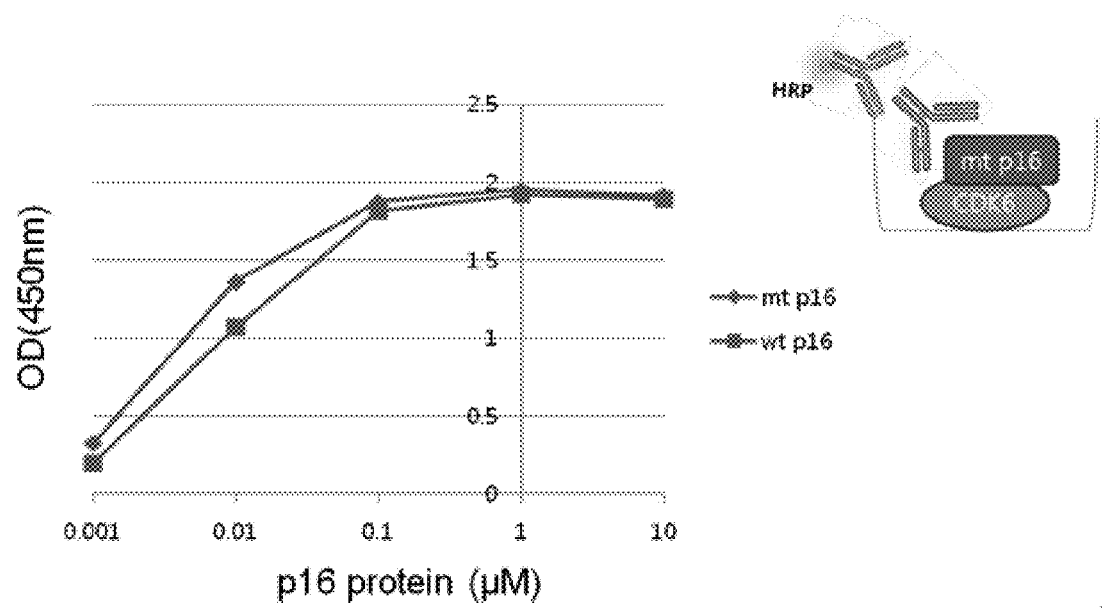
FIG. 5 is a graph showing the interaction of the p16 variant according to one embodiment with CDK6 as measured by ELISA (left), and illustrates an interaction process of p16, CDK6, and primary and secondary antibodies schematic view (right).

After complete removal of the washing solution, 100 μL of a TMB (tetramethylbenzidine) solution (Cell Signaling, Cat. Number: #7004L), as a chromogenic substrate, was added to each well. When a color developed to the desired intensity, 100 μL of a stop solution (Cell Signaling, Cat. Number: #7002L) was added, and absorbance at 450 nm was read on a microwell reader (Molecular Device, Model: 340PC384). For comparison, the p16 protein of SEQ ID NO: 1 (wild-type) was assayed for binding to Cdk6 in the same manner Results are given in FIG. 5. As apparent from the data of FIG. 5, the p16 protein variant (mt p16) retained affinity for the Cdk6 protein to the same degree as the wild-type p16 protein (wt p16), and behaved increased in affinity for the CDk6 protein in a concentration-dependent manner, like the wild-type p16 protein (wt p16).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A recombinant or synthetic p16 protein variant comprising a p16 protein in which at least one hydrophobic amino acid residue that is exposed on the tertiary structure of the p16 protein in aqueous solution is substituted with a hydrophilic amino acid, wherein the hydrophobic amino acid is leucine (L), cysteine (C), valine (V), phenyl alanine (F), tryptophan (W), isoleucine (I), proline (P), methionine (M), or a combination thereof; and the hydrophilic amino acid is lysine (K), aspartic acid (D), glutamic acid (E), glutamine (Q), asparagine (N), serine (S), alanine (A), threonine (T), arginine (R), or a combination thereof.

2. The recombinant or synthetic p16 protein variant of claim 1, wherein the p16 protein variant comprises a polypeptide having SEQ ID NO: 18, wherein at least one of $X_{20}$, $X_1$, $X_{16}$, and $X_{28}$ is independently selected from hydrophilic amino acids comprising lysine (K), aspartic acid (D), glutamic acid (E), glutamine (Q), asparagine (N), serine (S), alanine (A), threonine (T), and arginine (R).

3. The recombinant or synthetic p16 protein variant of claim 1, wherein the p16 protein variant comprises SEQ ID NO: 1 in which at least one of tryptophan at position 15 (W15), leucine at position 37 (L37), leucine at position 65 (L65), cysteine at position 72 (C72), leucine at position 78 (L78), valine at position 106 (V106) and leucine at position 113 (L113), of SEQ ID NO: 1, is independently substituted with lysine (K), aspartic acid (D), glutamic acid (E), glutamine (Q), asparagine (N), serine (S), alanine (A), threonine (T), or arginine (R).

4. The recombinant or synthetic p16 protein variant of claim 3, wherein the p16 protein variant comprises SEQ ID NO: 1 having at least one substitution selected from the group consisting of:
- a substitution of tryptophan at position 15 (W15) of SEQ ID NO: 1 with lysine (K), arginine (R), aspartic acid (D), glutamic acid (E), glutamine (Q), asparagine (N), or serine (S),
- a substitution of leucine at position 37 (L37) of SEQ ID NO: 1 with aspartic acid (D), arginine (R), lysine (K), glutamic acid (E), glutamine (Q), serine (S), or asparagine (N),
- a substitution of leucine at position 65 (L65) of SEQ ID NO: 1 with lysine (K), arginine (R), aspartic acid (D), glutamic acid (E), glutamine (Q), asparagine (N), or serine (S),
- a substitution of cysteine at position 72 (C72) of SEQ ID NO: 1 with serine (S),
- a substitution of leucine at position 78 (L78) of SEQ ID NO: 1 with serine (S), arginine (R), lysine (K), aspartic acid (D), glutamic acid (E), glutamine (Q), or asparagine (N),
- a substitution of valine at position 106 (V106) of SEQ ID NO: 1 with alanine (A), aspartic acid (D), glutamic acid (E), glutamine (Q), or asparagine (N), and
- a substitution of leucine at position 113 (L113) of SEQ ID NO: 1 with threonine (T), arginine (R), lysine (K), aspartic acid (D), glutamic acid (E), glutamine (Q), asparagine (N), or serine (S).

5. The recombinant or synthetic p16 protein variant of claim 4, in which cysteine at position 72 (C72) of SEQ ID NO: 1 is substituted with serine (S).

6. The recombinant or synthetic p16 protein variant of claim 5, wherein SEQ ID NO: 1 further comprises at least one substitution selected from the group consisting of:
- a substitution of tryptophan at position 15 (W15) of SEQ ID NO: 1 with lysine (K), arginine (R), aspartic acid (D), glutamic acid (E), glutamine (Q), asparagine (N), or serine (S),
- a substitution of leucine at position 65 (L65) of SEQ ID NO: 1 with lysine (K), arginine (R), aspartic acid (D), glutamic acid (E), glutamine (Q), asparagine (N), or serine (S), and
- a substitution of leucine at position 113 (L113) of SEQ ID NO: 1 with threonine (T), arginine (R), lysine (K), aspartic acid (D), glutamic acid (E), glutamine (Q), asparagine (N), or serine (S).

7. The recombinant or synthetic p16 protein variant of claim 6, wherein SEQ ID NO: 1 further comprises at least one substitution selected from the group consisting of:
- a substitution of leucine at position 37 (L37) of SEQ ID NO: 1 with aspartic acid (D), arginine (R), lysine (K), glutamic acid (E), glutamine (Q), serine (S), or asparagine (N),
- a substitution of leucine at position 78 (L78) of SEQ ID NO: 1 with serine (S), arginine (R), lysine (K), aspartic acid (D), glutamic acid (E), glutamine (Q), or asparagine (N), and
- a substitution of valine at position 106 (V106) of SEQ ID NO: 1 with alanine (A), aspartic acid (D), glutamic acid (E), glutamine (Q), or asparagine (N).

8. The recombinant or synthetic p16 protein variant of claim 1, comprising the amino acid sequence of SEQ ID NO: 2.

9. The recombinant or synthetic p16 protein variant of claim 1, wherein
the p16 protein variant comprises SEQ ID NO: 5 or SEQ ID NO: 6 in which at least one of an amino acid at position 64, an amino acid at position 70, an amino acid at position 98, and an amino acid at position 105, is independently substituted with lysine (K), aspartic acid (D), glutamic acid (E), glutamine (Q), asparagine (N), serine (S), alanine (A), threonine (T), or arginine (R).

10. A polynucleotide encoding the recombinant or synthetic p16 protein variant of claim 1.

11. The polynucleotide of claim 10 comprising the nucleotide sequence of SEQ ID NO: 3.

12. A recombinant vector comprising the polynucleotide of claim 10.

13. A recombinant cell comprising the recombinant vector of claim 12.

14. A pharmaceutical composition comprising the p16 protein variant of claim 1 and a carrier.

15. A method of providing a recombinant or synthetic p16 protein variant having increased solubility, comprising:
preparing a polypeptide comprising SEQ ID NO: 1 in which at least one of tryptophan at position 15(W15), leucine at position 37 (L37), leucine at position 65 (L65), cysteine at position 72 (C72), leucine at position 78 (L78), valine at position 106 (V106), and leucine at position 113 (L113), is independently substituted with lysine (K), aspartic acid (D), glutamic acid (E), glutamine (Q), asparagine (N), serine (S), alanine (A), threonine (T), or arginine (R), or
preparing a polypeptide comprising SEQ ID NO: 5 or 6 in which at least one of an amino acid at position 64, an amino acid at position 70, an amino acid at position 98, and an amino acid at position 105, is independently substituted with lysine (K), aspartic acid (D), glutamic acid (E), glutamine (Q), asparagine (N), serine (S), alanine (A), threonine (T), or arginine (R).

16. The method of claim 15, wherein the polypeptide is prepared by expressing a polynucleotide encoding the polypeptide in a cell.

17. A method of increasing solubility of a p15(INK4b), p16(INK4a), p18(INK4c), or p19(INK4d), the method comprising:
comparing solvent-exposed regions of the p15(INK4b), p16(INK4a), p18(INK4c), or p19(INK4d) protein and a reference designed ankyrin repeat protein (DARPin) comprising 4 or 5 ankyrin repeat motifs through secondary or tertiary structure-based alignment;
identifying a position of the solvent exposed region of the p15(INK4b), p16(INK4a), p18(INK4c), or p19 (INK4d) protein where the p15(INK4b), p16(INK4a), p18(INK4c), or p19(INK4d) protein has a hydrophobic amino acid while the reference DARPin protein has a hydrophilic amino acid at a corresponding position; and
substituting the hydrophobic amino acid at the position in the protein of interest with a hydrophilic amino acid,
wherein the hydrophobic amino acid is leucine (L), cysteine (C), valine (V), phenyl alanine (F), tryptophan (W), isoleucine (I), proline (P), methionine (M), or a combination thereof, and the hydrophilic amino acid is lysine (K), aspartic acid (D), glutamic acid (E), glutamine (Q), asparagine (N), serine (S), alanine (A), threonine (T), arginine (R), or a combination thereof.

* * * * *

SEQUENCE LISTING

<160> NUMBER OF SEQ ID NOS: 18

<210> SEQ ID NO 1
<211> LENGTH: 156
<212> TYPE: PRT
<213> ORGANISM: Artificial Sequence
<220> FEATURE:
<223> OTHER INFORMATION: Synthetic Amino Acid Sequence of Wild-Type
      Human p16

<400> SEQUENCE: 1

Met Glu Pro Ala Ala Gly Ser Ser Met Glu Pro Ser Ala Asp Trp Leu
 1               5                  10                  15

Ala Thr Ala Ala Ala Arg Gly Arg Val Glu Val Arg Ala Leu Leu
                20                  25                  30

Glu Ala Gly Ala Leu Pro Asn Ala Pro Asn Ser Tyr Gly Arg Arg Pro
            35                  40                  45

Ile Gln Val Met Met Met Gly Ser Ala Arg Val Ala Glu Leu Leu Leu
    50                  55                  60

Leu His Gly Ala Glu Pro Asn Cys Ala Asp Pro Ala Thr Leu Thr Arg
65                  70                  75                  80

Pro Val His Asp Ala Ala Arg Glu Gly Phe Leu Asp Thr Leu Val Val
                85                  90                  95

Leu His Arg Ala Gly Ala Arg Leu Asp Val Arg Asp Ala Trp Gly Arg
            100                 105                 110

Leu Pro Val Asp Leu Ala Glu Glu Leu Gly His Arg Asp Val Ala Arg
        115                 120                 125

Tyr Leu Arg Ala Ala Ala Gly Gly Thr Arg Gly Ser Asn His Ala Arg
    130                 135                 140

Ile Asp Ala Ala Glu Gly Pro Ser Asp Ile Pro Asp
145                 150                 155

<210> SEQ ID NO 2
<211> LENGTH: 156
<212> TYPE: PRT
<213> ORGANISM: Artificial Sequence
<220> FEATURE:
<223> OTHER INFORMATION: Synthetic Amino Acid Sequence of Human p16
      Variant

<400> SEQUENCE: 2

Met Glu Pro Ala Ala Gly Ser Ser Met Glu Pro Ser Ala Asp Lys Leu
 1               5                  10                  15

Ala Thr Ala Ala Ala Arg Gly Arg Val Glu Val Arg Ala Leu Leu
                20                  25                  30

Glu Ala Gly Ala Asp Pro Asn Ala Pro Asn Ser Tyr Gly Arg Arg Pro
            35                  40                  45

Ile Gln Val Met Met Met Gly Ser Ala Arg Val Ala Glu Leu Leu Leu
    50                  55                  60

Lys His Gly Ala Glu Pro Asn Ser Ala Asp Pro Ala Thr Ser Thr Arg
65                  70                  75                  80

Pro Val His Asp Ala Ala Arg Glu Gly Phe Leu Asp Thr Leu Val Val
                85                  90                  95

Leu His Arg Ala Gly Ala Arg Leu Asp Ala Arg Asp Ala Trp Gly Arg
            100                 105                 110

Thr Pro Val Asp Leu Ala Glu Glu Leu Gly His Arg Asp Val Ala Arg
        115                 120                 125

Tyr Leu Arg Ala Ala Ala Gly Gly Thr Arg Gly Ser Asn His Ala Arg

```
                    130                 135                 140
Ile Asp Ala Ala Glu Gly Pro Ser Asp Ile Pro Asp
145                 150                 155

<210> SEQ ID NO 3
<211> LENGTH: 468
<212> TYPE: DNA
<213> ORGANISM: Artificial Sequence
<220> FEATURE:
<223> OTHER INFORMATION: Synthetic DNA Sequence of human p16 variant

<400> SEQUENCE: 3
atggaaccgg ctgctggcag ctctatggaa ccgtctgctg acaaactggc taccgctgct      60
gctcgtggtc gtgttgaaga agttcgtgct ctgctggaag ctggtgctga tccgaacgct     120
ccgaactctt acggtcgtcg tccgatccag gttatgatga tgggcagcgc tcgtgttgct     180
gaactgctgc tgaaacacgg tgctgaaccg aacagcgctg acccggctac cagcacccgt     240
ccggttcacg acgctgctcg tgaaggtttc tggacacccc tggttgttct gcaccgtgct     300
ggtgctcgtc tggacgcgcg tgacgcttgg ggtcgtaccc cggttgacct ggctgaagaa     360
ctgggtcacc gtgacgttgc tcgttacctg cgtgctgctg ctggtggtac cgtggcagc     420 aaccacgctc gtatcgacgc tgctgaaggt ccgtctgaca tcccggac                  468

<210> SEQ ID NO 4
<211> LENGTH: 471
<212> TYPE: DNA
<213> ORGANISM: Artificial Sequence
<220> FEATURE:
<223> OTHER INFORMATION: Synthetic DNA sequence of wild-type human p16
      protein

<400> SEQUENCE: 4
atggagccgg cggcggggag cagcatggag ccttcggctg actggctggc cacggccgcg      60
gcccggggtc gggtagagga ggtgcgggcg ctgctgaggc ggggggcgct gcccaacgca     120
ccgaatagtt acggtcggag gccgatccag gtcatgatga tgggcagcgc ccgagtggcg     180
gagctgctgc tgctccacgg cgcggagccc aactgcgccg accccgccac tctcacccga     240
cccgtgcacg acgctgcccg ggagggcttc ctggacacgc tggtggtgct gcaccgggcc     300
ggggcgcggc tggacgtgcg cgatgcctgg ggccgtctgc ccgtggacct ggctgaggag     360
ctgggccatc gcgatgtcgc acggtacctg cgcgcggctg cggggggcac cagaggcagt     420
aaccatgccc gcatagatgc cgcggaaggt ccctcagaca tccccgattg a              471

<210> SEQ ID NO 5
<211> LENGTH: 168
<212> TYPE: PRT
<213> ORGANISM: Artificial Sequence
<220> FEATURE:
<223> OTHER INFORMATION: Synthetic mouse_p16

<400> SEQUENCE: 5

Met Glu Ser Ala Ala Asp Arg Leu Ala Arg Ala Ala Ala Gln Gly Arg
1               5                   10                  15

Val His Asp Val Arg Ala Leu Leu Glu Ala Gly Val Ser Pro Asn Ala
                20                  25                  30

Pro Asn Ser Phe Gly Arg Thr Pro Ile Gln Val Met Met Met Gly Asn
            35                  40                  45

Val His Val Ala Ala Leu Leu Leu Asn Tyr Gly Ala Asp Ser Asn Cys
        50                  55                  60
```

Glu Asp Pro Thr Thr Phe Ser Arg Pro Val His Asp Ala Ala Arg Glu
65                  70                  75                  80

Gly Phe Leu Asp Thr Leu Val Val Leu His Gly Ser Gly Ala Arg Leu
                85                  90                  95

Asp Val Arg Asp Ala Trp Gly Arg Leu Pro Leu Asp Leu Ala Gln Glu
            100                 105                 110

Arg Gly His Gln Asp Ile Val Arg Tyr Leu Arg Ser Ala Gly Cys Ser
        115                 120                 125

Leu Cys Ser Ala Gly Trp Ser Leu Cys Thr Ala Gly Asn Val Ala Gln
    130                 135                 140

Thr Asp Gly His Ser Phe Ser Ser Thr Pro Arg Ala Leu Glu Leu
145                 150                 155                 160

Arg Gly Gln Ser Gln Glu Gln Ser
                165

<210> SEQ ID NO 6
<211> LENGTH: 159
<212> TYPE: PRT
<213> ORGANISM: Artificial Sequence
<220> FEATURE:
<223> OTHER INFORMATION: Synthetic rat_p16

<400> SEQUENCE: 6

Met Glu Ser Ser Ala Asp Arg Leu Ala Arg Ala Ala Leu Gly Arg
1               5                   10                  15

Glu His Glu Val Arg Ala Leu Leu Glu Ala Gly Ala Ser Pro Asn Ala
                20                  25                  30

Pro Asn Thr Phe Gly Arg Thr Pro Ile Gln Val Met Met Met Gly Asn
            35                  40                  45

Val Lys Val Ala Ala Leu Leu Ser Tyr Gly Ala Asp Ser Asn Cys
        50                  55                  60

Glu Asp Pro Thr Thr Leu Ser Arg Pro Val His Asp Ala Ala Arg Glu
65                  70                  75                  80

Gly Phe Leu Asp Thr Leu Val Val Leu His Gln Ala Gly Ala Arg Leu
                85                  90                  95

Asp Val Arg Asp Ala Trp Gly Arg Leu Pro Leu Asp Leu Ala Leu Glu
            100                 105                 110

Arg Gly His His Asp Val Val Arg Tyr Leu Arg Tyr Leu Leu Ser Ser
        115                 120                 125

Ala Gly Asn Val Ser Arg Val Thr Asp Arg His Asn Phe Cys Ser Ser
    130                 135                 140

Thr Pro Arg Cys Leu Gly Leu Arg Gly Gln Pro Pro Lys Gln Arg
145                 150                 155

<210> SEQ ID NO 7
<211> LENGTH: 136
<212> TYPE: PRT
<213> ORGANISM: Artificial Sequence
<220> FEATURE:
<223> OTHER INFORMATION: Synthetic 4 ANK repeat DARPin 3HG0
<220> FEATURE:
<221> NAME/KEY: PEPTIDE
<222> LOCATION: (1)..(10)
<223> OTHER INFORMATION: N-terminal His tag for purification

<400> SEQUENCE: 7

Met Arg Gly Ser His His His His His His Gly Ser Asp Leu Gly Lys
1               5                   10                  15

```
Lys Leu Leu Glu Ala Ala Arg Ala Gly Gln Asp Asp Glu Val Arg Ile
            20                  25                  30

Leu Met Ala Asn Gly Ala Asp Val Asn Ala Glu Asp Lys Val Gly Leu
        35                  40                  45

Thr Pro Leu His Leu Ala Ala Met Asn Asp His Leu Glu Ile Val Glu
    50                  55                  60

Val Leu Leu Lys Asn Gly Ala Asp Val Asn Ala Ile Asp Ala Ile Gly
65                  70                  75                  80

Glu Thr Pro Leu His Leu Val Ala Met Tyr Gly His Leu Glu Ile Val
                85                  90                  95

Glu Val Leu Leu Lys His Gly Ala Asp Val Asn Ala Gln Asp Lys Phe
            100                 105                 110

Gly Lys Thr Ala Phe Asp Ile Ser Ile Asp Asn Gly Asn Glu Asp Leu
        115                 120                 125

Ala Glu Ile Leu Gln Lys Leu Asn
    130                 135

<210> SEQ ID NO 8
<211> LENGTH: 136
<212> TYPE: PRT
<213> ORGANISM: Artificial Sequence
<220> FEATURE:
<223> OTHER INFORMATION: Synthetic 4 ANK repeat DARPin 2Y0B
<220> FEATURE:
<221> NAME/KEY: PEPTIDE
<222> LOCATION: (1)..(10)
<223> OTHER INFORMATION: N-terminal His tag for purification

<400> SEQUENCE: 8

Met Arg Gly Ser His His His His His His Gly Ser Asp Leu Gly Lys
1               5                   10                  15

Lys Leu Leu Glu Ala Thr Arg Ala Gly Gln Asp Glu Val Arg Ile
            20                  25                  30

Leu Met Ala Asn Gly Ala Asp Val Asn Ala Met Asp Asp Ala Gly Val
        35                  40                  45

Thr Pro Leu His Leu Ala Ala Lys Arg Gly His Leu Glu Ile Val Glu
    50                  55                  60

Val Leu Leu Lys His Gly Ala Asp Val Asn Ala Arg Asp Ile Trp Gly
65                  70                  75                  80

Arg Thr Pro Leu His Leu Ala Ala Thr Val Gly His Leu Glu Ile Val
                85                  90                  95

Glu Val Leu Leu Glu Tyr Gly Ala Asp Val Asn Ala Gln Asp Lys Phe
            100                 105                 110

Gly Lys Thr Ala Phe Asp Ile Ser Ile Asp Asn Gly Asn Glu Asp Leu
        115                 120                 125

Ala Glu Ile Leu Gln Lys Leu Asn
    130                 135

<210> SEQ ID NO 9
<211> LENGTH: 136
<212> TYPE: PRT
<213> ORGANISM: Artificial Sequence
<220> FEATURE:
<223> OTHER INFORMATION: Synthetic 4 ANK repeat DARPin 2XZT
<220> FEATURE:
<221> NAME/KEY: PEPTIDE
<222> LOCATION: (1)..(10)
<223> OTHER INFORMATION: N-terminal His tag for purification

<400> SEQUENCE: 9
```

Met Arg Gly Ser His His His His His Gly Ser Asp Leu Gly Lys
1               5                   10                  15

Lys Leu Leu Glu Ala Thr Arg Ala Gly Gln Asp Asp Glu Val Arg Ile
            20                  25                  30

Leu Met Ala Asn Gly Ala Asp Val Asn Ala Met Asp Asp Ala Gly Val
        35                  40                  45

Thr Pro Leu His Leu Ala Ala Lys Arg Gly His Leu Glu Ile Val Glu
    50                  55                  60

Val Leu Leu Lys His Gly Ala Asp Val Asn Ala Ser Asp Ser Trp Gly
65              70                  75                  80

Arg Thr Pro Leu His Leu Ala Ala Thr Val Gly His Leu Glu Ile Val
            85                  90                  95

Glu Val Leu Leu Glu Tyr Gly Ala Asp Val Asn Ala Gln Asp Lys Phe
            100                 105                 110

Gly Lys Thr Ala Phe Asp Ile Ser Ile Asp Asn Gly Asn Glu Asp Leu
            115                 120                 125

Ala Glu Ile Leu Gln Lys Leu Asn
    130                 135

<210> SEQ ID NO 10
<211> LENGTH: 136
<212> TYPE: PRT
<213> ORGANISM: Artificial Sequence
<220> FEATURE:
<223> OTHER INFORMATION: Synthetic 4 ANK repeat DARPin 2XZD
<220> FEATURE:
<221> NAME/KEY: PEPTIDE
<222> LOCATION: (1)..(10)
<223> OTHER INFORMATION: N-terminal His tag for purification

<400> SEQUENCE: 10

Met Arg Gly Ser His His His His His Gly Ser Asp Leu Gly Lys
1               5                   10                  15

Lys Leu Leu Glu Ala Thr Arg Ala Gly Gln Asp Asp Glu Val Arg Ile
            20                  25                  30

Leu Met Ala Asn Gly Ala Asp Val Asn Ala Met Asp Asp Ala Gly Val
        35                  40                  45

Thr Pro Leu His Leu Ala Ala Lys Arg Gly His Leu Glu Ile Val Glu
    50                  55                  60

Val Leu Leu Lys His Gly Ala Asp Val Asn Ala Ser Asp Ile Trp Gly
65              70                  75                  80

Arg Thr Pro Leu His Leu Ala Ala Thr Val Gly His Leu Glu Ile Val
            85                  90                  95

Glu Val Leu Leu Glu Tyr Gly Ala Asp Val Asn Ala Gln Asp Lys Phe
            100                 105                 110

Gly Lys Thr Ala Phe Asp Ile Ser Ile Asp Asn Gly Asn Glu Asp Leu
            115                 120                 125

Ala Glu Ile Leu Gln Lys Leu Asn
    130                 135

<210> SEQ ID NO 11
<211> LENGTH: 136
<212> TYPE: PRT
<213> ORGANISM: Artificial Sequence
<220> FEATURE:
<223> OTHER INFORMATION: Synthetic 4 ANK repeat DARPin 2V4H
<220> FEATURE:
<221> NAME/KEY: PEPTIDE
<222> LOCATION: (1)..(10)
<223> OTHER INFORMATION: N-terminal His tag for purification

<400> SEQUENCE: 11

His His His His His His His His Gly Ser Asp Leu Gly Lys
 1               5                  10                  15

Lys Leu Leu Glu Ala Ala Arg Ala Gly Gln Asp Asp Glu Val Arg Ile
             20                  25                  30

Leu Met Ala Asn Gly Ala Asp Val Asn Ala Asn Asp Arg Lys Gly Asn
             35                  40                  45

Thr Pro Leu His Leu Ala Ala Asp Tyr Asp His Leu Glu Ile Val Glu
     50                  55                  60

Val Leu Leu Lys His Gly Ala Asp Val Asn Ala His Asp Asn Asp Gly
 65                  70                  75                  80

Ser Thr Pro Leu His Leu Ala Ala Leu Phe Gly His Leu Glu Ile Val
             85                  90                  95

Glu Val Leu Leu Lys His Gly Ala Asp Val Asn Ala Gln Asp Lys Phe
             100                 105                 110

Gly Lys Thr Ala Phe Asp Ile Ser Ile Asp Asn Gly Asn Glu Asp Leu
             115                 120                 125

Ala Glu Ile Leu Gln Lys Leu Asn
             130                 135

<210> SEQ ID NO 12
<211> LENGTH: 169
<212> TYPE: PRT
<213> ORGANISM: Artificial Sequence
<220> FEATURE:
<223> OTHER INFORMATION: Synthetic 5 ANK repeat DARPin 2Y1L
<220> FEATURE:
<221> NAME/KEY: PEPTIDE
<222> LOCATION: (1)..(10)
<223> OTHER INFORMATION: N-terminal His tag for purification

<400> SEQUENCE: 12

Met Arg Gly Ser His His His His His Gly Ser Asp Leu Gly Lys
 1               5                  10                  15

Lys Leu Leu Glu Ala Ala Arg Ala Gly Arg Asp Asp Glu Val Arg Ile
             20                  25                  30

Leu Met Ala Asn Gly Ala Asp Val Asn Ala Glu Asp Ala Ser Gly Trp
             35                  40                  45

Thr Pro Leu His Leu Ala Ala Phe Asn Gly His Leu Glu Ile Val Glu
     50                  55                  60

Val Leu Leu Lys Asn Gly Ala Asp Val Asn Ala Val Asp His Ala Gly
 65                  70                  75                  80

Met Thr Pro Leu Arg Leu Ala Ala Leu Phe Gly His Leu Glu Ile Val
             85                  90                  95

Glu Val Leu Leu Lys Asn Gly Ala Asp Val Asn Ala Asn Asp Met Glu
             100                 105                 110

Gly His Thr Pro Leu His Leu Ala Ala Met Phe Gly His Leu Glu Ile
             115                 120                 125

Val Glu Val Leu Leu Lys Asn Gly Ala Asp Val Asn Ala Gln Asp Lys
     130                 135                 140

Phe Gly Lys Thr Ala Phe Asp Ile Ser Ile Asp Asn Gly Asn Glu Asp
145                 150                 155                 160

Leu Ala Glu Ile Leu Gln Lys Leu Asn
             165

<210> SEQ ID NO 13

<211> LENGTH: 169
<212> TYPE: PRT
<213> ORGANISM: Artificial Sequence
<220> FEATURE:
<223> OTHER INFORMATION: Synthetic 5 ANK repeat DARPin 2J8S
<220> FEATURE:
<221> NAME/KEY: PEPTIDE
<222> LOCATION: (1)..(10)
<223> OTHER INFORMATION: N-terminal His tag for purification

<400> SEQUENCE: 13

```
Met Arg Gly Ser His His His His His Gly Ser Asp Leu Gly Lys
  1               5                  10                  15

Lys Leu Leu Glu Ala Ala Arg Ala Gly Arg Asp Asp Glu Val Arg Ile
                 20                  25                  30

Leu Met Ala Asn Gly Ala Asp Val Asn Ala Ala Asp Val Val Gly Trp
             35                  40                  45

Thr Pro Leu His Leu Ala Ala Tyr Trp Gly His Leu Glu Ile Val Glu
         50                  55                  60

Val Leu Leu Lys Asn Gly Ala Asp Val Asn Ala Tyr Asp Thr Leu Gly
 65                  70                  75                  80

Ser Thr Pro Leu His Leu Ala Ala His Phe Gly His Leu Glu Ile Val
                 85                  90                  95

Glu Val Leu Leu Lys Asn Gly Ala Asp Val Asn Ala Lys Asp Asp Asn
                100                 105                 110

Gly Ile Thr Pro Leu His Leu Ala Ala Asn Arg Gly His Leu Glu Ile
            115                 120                 125

Val Glu Val Leu Leu Lys Tyr Gly Ala Asp Val Asn Ala Gln Asp Lys
        130                 135                 140

Phe Gly Lys Thr Ala Phe Asp Ile Ser Ile Asn Asn Gly Asn Glu Asp
145                 150                 155                 160

Leu Ala Glu Ile Leu Gln Lys Leu Asn
                165
```

<210> SEQ ID NO 14
<211> LENGTH: 169
<212> TYPE: PRT
<213> ORGANISM: Artificial Sequence
<220> FEATURE:
<223> OTHER INFORMATION: Synthetic 5 ANK repeat DARPin 4DX6
<220> FEATURE:
<221> NAME/KEY: PEPTIDE
<222> LOCATION: (1)..(10)
<223> OTHER INFORMATION: N-terminal His tag for purification

<400> SEQUENCE: 14

```
Met Arg Gly Ser His His His His His Gly Ser Asp Leu Gly Lys
  1               5                  10                  15

Lys Leu Leu Glu Ala Ala Arg Ala Gly Arg Asp Asp Glu Val Arg Ile
                 20                  25                  30

Leu Met Ala Asn Gly Ala Asp Val Asn Ala Ala Asp Val Val Gly Trp
             35                  40                  45

Thr Pro Leu His Leu Ala Ala Tyr Trp Gly His Leu Glu Ile Val Glu
         50                  55                  60

Val Leu Leu Lys Asn Gly Ala Asp Val Asn Ala Tyr Asp Thr Leu Gly
 65                  70                  75                  80

Ser Thr Pro Leu His Leu Ala Ala His Phe Gly His Leu Glu Ile Val
                 85                  90                  95

Glu Val Leu Leu Lys Asn Gly Ala Asp Val Asn Ala Lys Asp Asp Asn
                100                 105                 110
```

```
Gly Ile Thr Pro Leu His Leu Ala Ala Asn Arg Gly His Leu Glu Ile
        115                 120                 125

Val Glu Val Leu Leu Lys Tyr Gly Ala Asp Val Asn Ala Gln Asp Lys
130                 135                 140

Phe Gly Lys Thr Ala Phe Asp Ile Ser Ile Asn Asn Gly Asn Glu Asp
145                 150                 155                 160

Leu Ala Glu Ile Leu Gln Lys Leu Asn
                165

<210> SEQ ID NO 15
<211> LENGTH: 169
<212> TYPE: PRT
<213> ORGANISM: Artificial Sequence
<220> FEATURE:
<223> OTHER INFORMATION: Synthetic 5 ANK repeat DARPin 4DRX
<220> FEATURE:
<221> NAME/KEY: PEPTIDE
<222> LOCATION: (1)..(10)
<223> OTHER INFORMATION: N-terminal His tag for purification

<400> SEQUENCE: 15

Met Arg Gly Ser His His His His His His Gly Ser Asp Leu Gly Lys
1               5                   10                  15

Lys Leu Leu Glu Ala Ala Arg Ala Gly Gln Asp Asp Glu Val Arg Ile
            20                  25                  30

Leu Met Ala Asn Gly Ala Asp Val Asn Ala Thr Asp Ala Ser Gly Leu
        35                  40                  45

Thr Pro Leu His Leu Ala Ala Thr Tyr Gly His Leu Glu Ile Val Glu
    50                  55                  60

Val Leu Lys His Gly Ala Asp Val Asn Ala Ile Asp Ile Met Gly
65                  70                  75                  80

Ser Thr Pro Leu His Leu Ala Ala Leu Ile Gly His Leu Glu Ile Val
                85                  90                  95

Glu Val Leu Leu Lys His Gly Ala Asp Val Asn Ala Val Asp Thr Trp
            100                 105                 110

Gly Asp Thr Pro Leu His Leu Ala Ala Ile Met Gly His Leu Glu Ile
        115                 120                 125

Val Glu Val Leu Leu Lys His Gly Ala Asp Val Asn Ala Gln Asp Lys
130                 135                 140

Phe Gly Lys Thr Ala Phe Asp Ile Ser Ile Asp Asn Gly Asn Glu Asp
145                 150                 155                 160

Leu Ala Glu Ile Leu Gln Lys Leu Asn
                165

<210> SEQ ID NO 16
<211> LENGTH: 169
<212> TYPE: PRT
<213> ORGANISM: Artificial Sequence
<220> FEATURE:
<223> OTHER INFORMATION: Synthetic 5 ANK repeat DARPin 2P2C
<220> FEATURE:
<221> NAME/KEY: PEPTIDE
<222> LOCATION: (1)..(10)
<223> OTHER INFORMATION: N-terminal His tag for purification

<400> SEQUENCE: 16

Met Arg Gly Ser His His His His His His Gly Ser Asp Leu Gly Lys
1               5                   10                  15

Lys Leu Leu Glu Ala Ala Arg Ala Gly Gln Asp Asp Glu Val Arg Ile
            20                  25                  30
```

```
Leu Met Ala Asn Gly Ala Asp Val Asn Ala Thr Asp Trp Leu Gly His
            35                  40                  45

Thr Pro Leu His Leu Ala Ala Lys Thr Gly His Leu Glu Ile Val Glu
     50                  55                  60

Val Leu Leu Lys Tyr Gly Ala Asp Val Asn Ala Trp Asp Asn Tyr Gly
 65                  70                  75                  80

Ala Thr Pro Leu His Leu Ala Ala Asp Asn Gly His Leu Glu Ile Val
                 85                  90                  95

Glu Val Leu Leu Lys His Gly Ala Asp Val Asn Ala Lys Asp Tyr Glu
            100                 105                 110

Gly Phe Thr Pro Leu His Leu Ala Ala Tyr Asp Gly His Leu Glu Ile
            115                 120                 125

Val Glu Val Leu Leu Lys Tyr Gly Ala Asp Val Asn Ala Gln Asp Lys
        130                 135                 140

Phe Gly Lys Thr Ala Phe Asp Ile Ser Ile Asp Asn Gly Asn Glu Asp
145                 150                 155                 160

Leu Ala Glu Ile Leu Gln Lys Leu Asn
                165
```

<210> SEQ ID NO 17
<211> LENGTH: 169
<212> TYPE: PRT
<213> ORGANISM: Artificial Sequence
<220> FEATURE:
<223> OTHER INFORMATION: Synthetic 5 ANK repeat DARPin 3NOG
<220> FEATURE:
<221> NAME/KEY: PEPTIDE
<222> LOCATION: (1)..(10)
<223> OTHER INFORMATION: N-terminal His tag for purification

<400> SEQUENCE: 17

```
Met Arg Gly Ser His His His His His His Gly Ser Asp Leu Gly Lys
 1               5                  10                  15

Lys Leu Leu Glu Ala Ala Arg Ala Gly Gln Asp Asp Glu Val Arg Ile
             20                  25                  30

Leu Met Ala Asn Gly Ala Asp Val Asn Ala Ser Asp His Val Gly Trp
            35                  40                  45

Thr Pro Leu His Leu Ala Ala Tyr Phe Gly His Leu Glu Ile Val Glu
     50                  55                  60

Val Leu Leu Lys Asn Gly Ala Asp Val Asn Ala Asp Asp Ser Leu Gly
 65                  70                  75                  80

Val Thr Pro Leu His Leu Ala Ala Asp Arg Gly His Leu Glu Val Val
                 85                  90                  95

Glu Val Leu Leu Lys Asn Gly Ala Asp Val Asn Ala Asn Asp His Asn
            100                 105                 110

Gly Phe Thr Pro Leu His Leu Ala Ala Asn Ile Gly His Leu Glu Ile
            115                 120                 125

Val Glu Val Leu Leu Lys His Gly Ala Asp Val Asn Ala Gln Asp Lys
        130                 135                 140

Phe Gly Lys Thr Ala Phe Asp Ile Ser Ile Asp Asn Gly Asn Glu Asp
145                 150                 155                 160

Leu Ala Glu Ile Leu Gln Lys Leu Asn
                165
```

<210> SEQ ID NO 18
<211> LENGTH: 99
<212> TYPE: PRT
<213> ORGANISM: Artificial Sequence
<220> FEATURE:

```
<223> OTHER INFORMATION: Synthetic p16 protein variant
<220> FEATURE:
<221> NAME/KEY: MOD_RES
<222> LOCATION: (1)..(1)
<223> OTHER INFORMATION: Xaa is a hydrophilic amino acid or W, e.g.,
      K, R, D, E, Q, N, S, or W
<220> FEATURE:
<221> NAME/KEY: MOD_RES
<222> LOCATION: (4)..(4)
<223> OTHER INFORMATION: Xaa is T or R
<220> FEATURE:
<221> NAME/KEY: MOD_RES
<222> LOCATION: (8)..(8)
<223> OTHER INFORMATION: Xaa is R, Q, or L
<220> FEATURE:
<221> NAME/KEY: MOD_RES
<222> LOCATION: (11)..(11)
<223> OTHER INFORMATION: Xaa is V or E
<220> FEATURE:
<221> NAME/KEY: MOD_RES
<222> LOCATION: (12)..(12)
<223> OTHER INFORMATION: Xaa is E or H
<220> FEATURE:
<221> NAME/KEY: MOD_RES
<222> LOCATION: (13)..(13)
<223> OTHER INFORMATION: Xaa is E or D
<220> FEATURE:
<221> NAME/KEY: MOD_RES
<222> LOCATION: (22)..(22)
<223> OTHER INFORMATION: Xaa is A or V
<220> FEATURE:
<221> NAME/KEY: MOD_RES
<222> LOCATION: (23)..(23)
<223> OTHER INFORMATION: Xaa is a hydrophilic amino acid or L, e.g.,
      D, R, K, E, Q, S, N, or L
<220> FEATURE:
<221> NAME/KEY: MOD_RES
<222> LOCATION: (29)..(29)
<223> OTHER INFORMATION: Xaa is S or T
<220> FEATURE:
<221> NAME/KEY: MOD_RES
<222> LOCATION: (30)..(30)
<223> OTHER INFORMATION: Xaa is Y or F
<220> FEATURE:
<221> NAME/KEY: MOD_RES
<222> LOCATION: (33)..(33)
<223> OTHER INFORMATION: Xaa is R or T
<220> FEATURE:
<221> NAME/KEY: MOD_RES
<222> LOCATION: (42)..(42)
<223> OTHER INFORMATION: Xaa is S or N
<220> FEATURE:
<221> NAME/KEY: MOD_RES
<222> LOCATION: (43)..(43)
<223> OTHER INFORMATION: Xaa is A or V
<220> FEATURE:
<221> NAME/KEY: MOD_RES
<222> LOCATION: (44)..(44)
<223> OTHER INFORMATION: Xaa is R, H, or K
<220> FEATURE:
<221> NAME/KEY: MOD_RES
<222> LOCATION: (47)..(47)
<223> OTHER INFORMATION: Xaa is E or A
<220> FEATURE:
<221> NAME/KEY: MOD_RES
<222> LOCATION: (51)..(51)
<223> OTHER INFORMATION: Xaa is a hydrophilic amino acid or L, e.g.,
      D, R, K, E, Q, S, N, or L
<220> FEATURE:
<221> NAME/KEY: MOD_RES
<222> LOCATION: (52)..(52)
<223> OTHER INFORMATION: Xaa is H or Y
<220> FEATURE:
<221> NAME/KEY: MOD_RES
<222> LOCATION: (55)..(55)
<223> OTHER INFORMATION: Xaa18 is E or D
<220> FEATURE:
<221> NAME/KEY: MOD_RES
<222> LOCATION: (56)..(56)
```

```
<223> OTHER INFORMATION: Xaa is P or S
<220> FEATURE:
<221> NAME/KEY: MOD_RES
<222> LOCATION: (58)..(58)
<223> OTHER INFORMATION: Xaa is a hydrophilic amino acid or C, e.g.,
      S or C
<220> FEATURE:
<221> NAME/KEY: MOD_RES
<222> LOCATION: (59)..(59)
<223> OTHER INFORMATION: Xaa is A or E
<220> FEATURE:
<221> NAME/KEY: MOD_RES
<222> LOCATION: (62)..(62)
<223> OTHER INFORMATION: Xaa is A or T
<220> FEATURE:
<221> NAME/KEY: MOD_RES
<222> LOCATION: (64)..(64)
<223> OTHER INFORMATION: Xaa is a hydrophilic amino acid, L, or F, e.g.,
      S, R, K, D, E, Q, N, L, or F
<220> FEATURE:
<221> NAME/KEY: MOD_RES
<222> LOCATION: (65)..(65)
<223> OTHER INFORMATION: Xaa is T or S
<220> FEATURE:
<221> NAME/KEY: MOD_RES
<222> LOCATION: (85)..(85)
<223> OTHER INFORMATION: Xaa is R, G, or Q
<220> FEATURE:
<221> NAME/KEY: MOD_RES
<222> LOCATION: (86)..(86)
<223> OTHER INFORMATION: Xaa is A or S
<220> FEATURE:
<221> NAME/KEY: MOD_RES
<222> LOCATION: (92)..(92)
<223> OTHER INFORMATION: Xaa is a hydrophilic amino acid or V, e.g.,
      A, D, E, Q, N, or V
<220> FEATURE:
<221> NAME/KEY: MOD_RES
<222> LOCATION: (99)..(99)
<223> OTHER INFORMATION: Xaa is a hydrophilic amino acid or L, e.g.,
      T, R, K, D, E, Q, N, S, or L

<400> SEQUENCE: 18

Xaa Leu Ala Xaa Ala Ala Ala Xaa Gly Arg Xaa Xaa Xaa Val Arg Ala
 1               5                  10                  15

Leu Leu Glu Ala Gly Xaa Xaa Pro Asn Ala Pro Asn Xaa Xaa Gly Arg
            20                  25                  30

Xaa Pro Ile Gln Val Met Met Met Gly Xaa Xaa Xaa Val Ala Xaa Leu
        35                  40                  45

Leu Leu Xaa Xaa Gly Ala Xaa Xaa Asn Xaa Xaa Asp Pro Xaa Thr Xaa
    50                  55                  60

Xaa Arg Pro Val His Asp Ala Ala Arg Glu Gly Phe Leu Asp Thr Leu
65                  70                  75                  80

Val Val Leu His Xaa Xaa Gly Ala Arg Leu Asp Xaa Arg Asp Ala Trp
                85                  90                  95

Gly Arg Xaa
```